(12) United States Patent
Bosmans et al.

(10) Patent No.: US 9,771,335 B2
(45) Date of Patent: *Sep. 26, 2017

(54) DERIVATIVES OF RUFINAMIDE AND THEIR USE IN INHIBTION OF THE ACTIVATION OF HUMAN VOLTAGE-GATED SODIUM CHANNELS

(71) Applicant: THE JOHNS HOPKINS UNIVERSITY, Baltimore, MD (US)

(72) Inventors: Frank Bosmans, Annapolis, MD (US); Jeet Kalia, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/814,702

(22) Filed: Jul. 31, 2015

(65) Prior Publication Data

US 2017/0029382 A1 Feb. 2, 2017

(51) Int. Cl.
*A61K 31/4192* (2006.01)
*C07D 249/04* (2006.01)
*A61K 45/06* (2006.01)

(52) U.S. Cl.
CPC ........ *C07D 249/04* (2013.01); *A61K 31/4192* (2013.01); *A61K 45/06* (2013.01)

(58) Field of Classification Search
None
See application file for complete search history.

(56) References Cited

U.S. PATENT DOCUMENTS 4,450,150 A 5/1984 Sidman
2008/0293737 A1* 11/2008 Martinborough ..... C07C 311/51
514/253.06
2009/0054414 A1* 2/2009 Woiwode ........... A61K 31/4192
514/221

FOREIGN PATENT DOCUMENTS

WO 2014120994 A1 8/2014

OTHER PUBLICATIONS

Arava et al., Der Pharma Chemica, 2011, 3(1): 381-387.*
Gilchrist et al., ACS Chem. Biol.; 2014, vol. 9, pp. 1204-1212.*
Dutton et al (2013) Preferential inactivation of Scn1a in parvalbumin interneurons increases seizure susceptibility. Neurobiol Dis. Jan. 2013;49:211-20. doi: 10.1016/j.nbd.2012.08.012. Epub Aug. 25, 2012.
Barton et al (2001) Pharmacological characterization of the 6 Hz psychomotor seizure model of partial epilepsy. Epilepsy Res. Dec. 2001;47(3):217-27.

* cited by examiner

*Primary Examiner* — Alicia L Otton
(74) *Attorney, Agent, or Firm* — John Hopkins Technology Transfer

(57) ABSTRACT

The present invention provides compounds of formula I which are capable of inhibition of the activation of hNav1.1 or hNav1.6 sodium channels in neurons. Pharmaceutical compositions comprising these compounds are also provided. Methods for prevention and treatment of neurological disorders, including, for example, seizures and seizure disorders, including Lennox-Gastaut Syndrome, Dravet syndrome, epileptic encephalopathies, autism, Familial hemiplegic migraine (FHM), anxiety disorders, including Post-traumatic stress disorder (PTSD), panic disorder and obsessive-compulsive disorder, neuropathic pain, and Rett syndrome by administration of these compounds are also provided.

22 Claims, 16 Drawing Sheets

DERIVATIVES OF RUFINAMIDE AND THEIR USE IN INHIBTION OF THE ACTIVATION OF HUMAN VOLTAGE-GATED SODIUM CHANNELS

BACKGROUND OF THE INVENTION

Lennox-Gastaut Syndrome (LGS) is a severe pediatric epilepsy disorder associated with various types of seizures and cognitive dysfunction that persist into adulthood. As a result, LGS patients suffer from varying degrees of learning disabilities, psychiatric disorders, and behavioral disturbances that can drastically affect their social integration. Diagnosis and ensuing management of LGS is challenging, relying mostly on the expertise of the treating physician to interpret an intricate amalgamation of clinical and EEG abnormalities. Although limited clinical trials suggest that a small subset of available anti-epileptic drugs such as lamotrigine, valproic acid, topiramate, felbamate, and clobazam may be used to manage the multiple seizure types associated with LGS, their efficacy is often inadequate and perilous adverse effects (AEs) may occur. The relatively new drug rufinamide, a compound with orphan drug status in the USA (2004) and marketing authorization in Europe (2007), displays a broad spectrum of anti-epileptic activity and clinical trials have demonstrated long-term beneficial effects and good tolerability when used as adjunctive therapy in children and adult LGS patients.

Lennox-Gastaut Syndrome (LGS) is a severe form of epilepsy manifesting during early childhood. Treatment of the seizures and the ensuing behavioral and mental health problems commonly associated with LGS requires multiple anticonvulsant therapeutics, often with deleterious effects on the patient. Although the relatively new orphan drug rufinamide is gaining importance as an adjunct therapy for LGS, its mode of action remains speculative.

Anomalous hNav1.1 behavior (www.molgen.vib-ua.be/scnlamutations/) have been implicated in Lennox-Gastaut Syndrome as well as partial or refractory focal seizures.

Given their unique role in electrical signaling and subsequent implications in various epilepsy disorders, voltage-gated sodium (Nav) channels within the central nervous system (CNS) are influenced by anti-epileptic drugs (AEDs). Of the nine Nav channel isoforms (Nav1.1-Nav1.9) identified in humans, four are expressed predominantly in the CNS (Nav1.1 (SCN1A), Nav1.2 (SCN2A), Nav1.3 (SCN3A), and Nav1.6 (SCN8A)). Supporting their physiological importance, mutations in Nav1.1 (more than 1200), Nav1.2, and Nav1.6 have been linked to various epilepsy phenotypes whereas Nav1.3 is believed to also be involved in nociception after channel upregulation due to spinal cord injury.

As such, there still exists an unmet need to understand the mechanism of action of voltage-gated sodium (Nav) in various neurological diseases and discovery of better and more efficacious drugs to treat LGS and other epilepsy related diseases.

SUMMARY OF THE INVENTION

In accordance with an embodiment, the present invention provides a novel group of compounds having specificity for inhibition of human Nav1.1 and hNav1.6 activation, a distinct working mechanism among anticonvulsants and a feature worth exploring for treating a growing number of other debilitating neurological disorders involving hNav1.1 and hNav1.6, including, for example, seizures and seizure disorders, including Lennox-Gastaut Syndrome, Dravet syndrome, epileptic encephalopathies, autism, Familial hemiplegic migraine (FHM), anxiety disorders, including Post-traumatic stress disorder (PTSD), panic disorder and obsessive-compulsive disorder, neuropathic pain, and Rett syndrome.

Subsequent structure-activity relationship experiments with related N-benzyl triazole compounds revealed at least one or more novel drug variants that: 1) shifts hNav1.1 and hNav1.6 opening to more depolarized voltages without altering other channel gating properties; 2) increases the threshold to action potential initiation in hippocampal neurons; and 3) greatly reduces seizures in three animal models.

The present inventors set out to investigate whether rufinamide influences the functional properties of one or more of four Nav channel isoforms. To this end, the inventors first had to overcome drug solubility issues and the hurdle of expressing human (h)Nav1.1, hNav1.2, hNav1.3, and hNav1.6 in a heterologous expression system, obstacles that were overcome successfully. As a result, the inventors found that a clinically relevant rufinamide concentration dramatically inhibits hNav1.1 and hNav1.6 activation whereas the recovery from fast inactivation of hNav1.1, hNav1.2, hNav1.3, and hNav1.6 is slightly altered. Moreover, experiments with structurally related compounds reveal that chemical derivatization at particular positions on the triazole pharmacophore can be exploited to obtain an isoform-specific drug-induced inhibition of hNav1.1 and/or hNav1.6 activation. This information was described in detail in the inventors' previous work (International Patent Publication No. WO 2014/120994) incorporated by reference herein.

As a result, it was found that rufinamide specifically inhibits hNav1.1 activation whereas the recovery from fast inactivation of hNav1.1, hNav1.2, hNav1.3, and hNav1.6 is slowed down. Moreover, experiments with related triazole compounds revealed a series of more efficacious drug variants, thus providing important molecular insights into rational drug design efforts on the N-benzyl triazole scaffold of rufinamide for developing hNav channel isoform-specific drugs.

Therefore, in accordance with an embodiment, the present invention provides a compound of formula I:

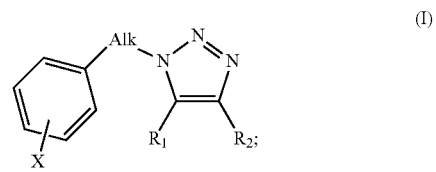

or a salt, solvate, or stereoisomer thereof, wherein X is H, or one or more electron withdrawing groups such as a halogen, $NH_2$, $NO_2$, $SO_2$, CN, or a $C_1$-$C_6$ alkyl group; Alk is $C_1$-$C_3$ alkyl; $R_1$ is H, $C_1$-$C_6$ alkyl, which may be substituted with OH, $NH_2$, alkylamino, amido, acyl, sulfonyl, sulfonylamino, and cyano groups; and $R_2$, is $C_1$-$C_6$ alkyl, alkenyl, and phenyl, which may be substituted with one or more OH, $NH_2$, alkylamino, amido, acyl, carboxyl, methoxyl, sulfonyl, and cyano groups.

In accordance with another embodiment, the present invention provides the compounds of formula I selected from the group consisting of:

(Compound A)
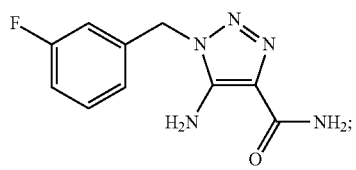
(Compound B)
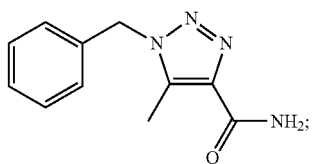
(Compound C)
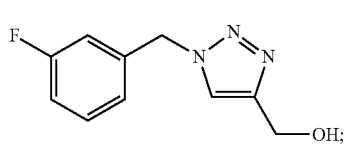
(Compound D)
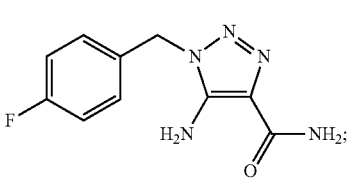
(Compound E)
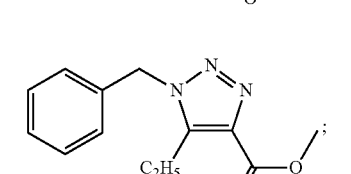
(Compound F)
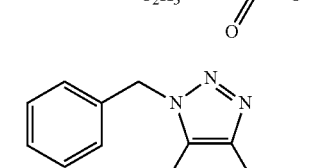
(Compound G)
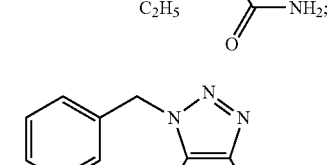
(Compound H)
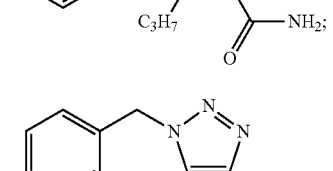
(Compound I)
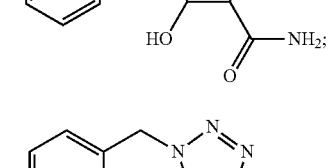
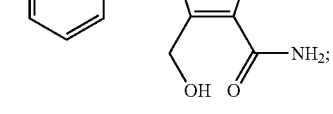
(Compound J)
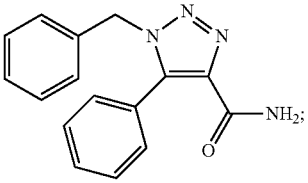
(Compound K)
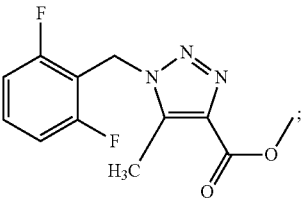
(Compound L)
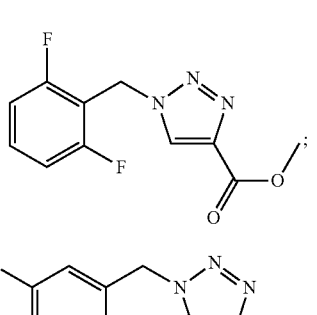
(Compound M)
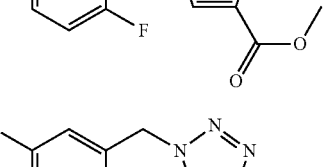
(Compound N)
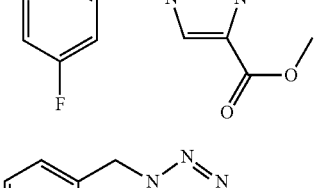
(Compound O)
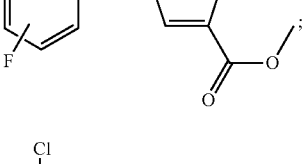
(Compound P)
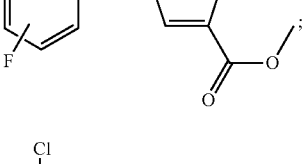
(Compound Q)
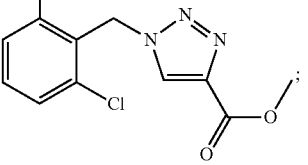
or a salt, solvate, or stereoisomer thereof.
In accordance with a further embodiment, the present invention provides a pharmaceutical composition comprising a compound, salt, solvate, or stereoisomer of any of the compounds described herein, and a pharmaceutically acceptable carrier.

In accordance with an embodiment, the present invention provides a pharmaceutical composition comprising a compound, salt, solvate, or stereoisomer of any of the compounds described herein, wherein the composition further comprises at least one additional therapeutic agent.

In accordance with another embodiment, the present invention provides a pharmaceutical composition comprising a compound of formula I:

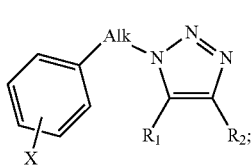

(I)

or a salt, solvate, or stereoisomer thereof, wherein X is H, or one or more electron withdrawing groups such as a halogen, $NH_2$, $NO_2$, $SO_2$, CN, or a $C_1$-$C_6$ alkyl group; Alk is $C_1$-$C_3$ alkyl; $R_1$ is H, $C_1$-$C_6$ alkyl, which may be substituted with OH, $NH_2$, alkylamino, amido, acyl, sulfonyl, sulfonylamino, and cyano groups; and $R_2$, is $C_1$-$C_6$ alkyl, alkenyl, and phenyl, which may be substituted with one or more OH, $NH_2$, alkylamino, amido, acyl, carboxyl, methoxyl, sulfonyl, and cyano groups, and a pharmaceutically acceptable carrier, in an effective amount, for use as a medicament, preferably for use in modulating the opening of one or more voltage-gated sodium hNav1.1 or hNav1.6 channels in one or more neurons of a subject, or for use in treating an neurological disorder in a subject.

In accordance with an embodiment, the present invention provides methods for inhibiting the activation of one or more voltage-gated sodium hNav1.1 and/or hNav1.6 channels in one or more neurons of a subject comprising contacting the one or more neurons with an effective amount of the compound or compositions described herein.

In accordance with an embodiment, the present invention provides a method for treating a neurological disorder in a subject comprising administering to the subject a therapeutically effective amount of the compound or compositions described herein.

In accordance with an embodiment, the present invention provides a method for treating a seizure disorder in a subject comprising administering to the subject a therapeutically effective amount of the compound or compositions described herein.

Left column shows G/G$_{max}$ (representing channel opening) whereas right column displays I/Imax (representing channel availability) relationships. The figure shows that 1-(phenylmethyl)-1H-1,2,3-triazole-4-carboxamide-5-ethyl (Compound F) inhibits hNav1.1 opening whereas the effect on other hNav channels is not significant compared to DMSO treatment of these isoforms (1% DMSO control is in black). All data is shown before (black—DMSO control) and after (red) addition of 100M 1-(phenylmethyl)-1H-1,2, 3-triazole-4-carboxamide-5-ethyl on hNav1.1, hNav1.2, hNav1.3, and hNav1.6. n=5-8 and error bars represent s.e.m.

Figure 16:
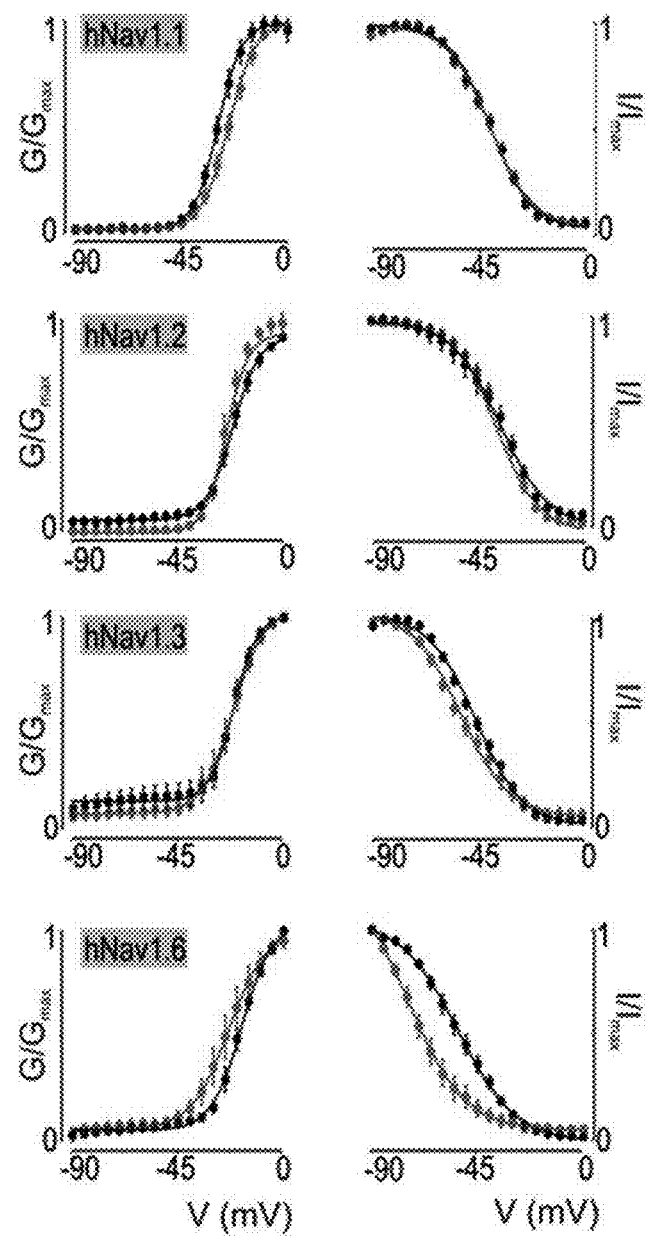

FIG. 16: Effects of Compound M on hNav1.6 channels.

Left column shows G/G$_{max}$ (representing channel opening) whereas right column displays I/Imax (representing channel availability) relationships. The figure shows that 1-[(2,6-difluorophenyl)methyl]-1H-1,2,3-triazole-carboxymethyl-5-methyl (Compound M) only slightly inhibits hNav1.1 opening whereas the effect on hNav1.2 and hNav1.3 channels is not significant compared to DMSO treatment of these isoforms (1% DMSO control is in black). The compound does dramatically affect hNav1.6 steady-state inactivation. All data is shown before (black—DMSO control) and after (red) addition of 100 µM 1-[(2,6-difluorophenyl)methyl]-1H-1,2,3-triazole-carboxymethyl-5-methyl on hNav1.1, hNav1.2, hNav1.3, and hNav1.6. n=5-8 and error bars represent s.e.m.

DETAILED DESCRIPTION OF THE INVENTION

In accordance with an embodiment, the present invention provides a compound of formula I:

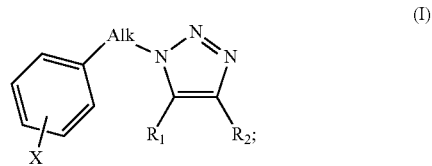

(I)

or a salt, solvate, or stereoisomer thereof, wherein X is H, or one or more electron withdrawing groups such as a halogen, NH$_2$, NO$_2$, SO$_2$, CN, or a C$_1$-C$_6$ alkyl group; Alk is C$_1$-C$_3$ alkyl; R$_1$ is H, C$_1$-C$_6$ alkyl, which may be substituted with OH, NH$_2$, alkylamino, amido, acyl, sulfonyl, sulfonylamino, and cyano groups; and R$_2$, is C$_1$-C$_6$ alkyl, alkenyl, and phenyl, which may be substituted with one or more OH, NH$_2$, alkylamino, amido, acyl, carboxyl, methoxyl, sulfonyl, and cyano groups.

As used herein, examples of the term "alkyl" preferably include a C$_{1-6}$ alkyl (e.g., methyl, ethyl, propyl, isopropyl, butyl, isobutyl, sec-butyl, tert-butyl, pentyl, hexyl, etc.) and the like.

As used herein, examples of the term "alkenyl" preferably include C$_{2-6}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl, etc.) and the like.

As used herein, examples of the term "alkynyl" preferably include C$_{2-6}$ alkynyl (e.g., ethynyl, propargyl, 1-butynyl, 2-butynyl, 3-butynyl, 1-hexynyl, etc.) and the like.

Examples of the term "aryl" preferably include a $C_{6-14}$ aryl (e.g., a phenyl, 1-naphthyl, a 2-naphthyl, 2-biphenylyl group, 3-biphenylyl, 4-biphenylyl, 2-anthracenyl, etc.) and the like.

Examples of the term "arylalkyl" preferably include a $C_{6-14}$ arylalkyl (e.g., benzyl, phenylethyl, diphenylmethyl, 1-naphthylmethyl, 2-naphthylmethyl, 2,2-diphenylethyl, 3-phenylpropyl, 4-phenylbutyl, 5-phenylpentyl, etc.) and the like.

The term "hydroxyalkyl" embraces linear or branched alkyl groups having one to about ten carbon atoms any one of which may be substituted with one or more hydroxyl groups.

The term "alkylamino" includes monoalkylamino. The term "monoalkylamino" means an amino, which is substituted with an alkyl as defined herein. Examples of monoalkylamino substituents include, but are not limited to, methylamino, ethylamino, isopropylamino, t-butylamino, and the like. The term "dialkylamino" means an amino, which is substituted with two alkyls as defined herein, which alkyls can be the same or different. Examples of dialkylamino substituents include dimethylamino, diethylamino, ethylisopropylamino, diisopropylamino, dibutylamino, and the like.

The terms "alkylthio," "alkenylthio" and "alkynylthio" mean a group consisting of a sulphur atom bonded to an alkyl-, alkenyl- or alkynyl-group, which is bonded via the sulphur atom to the entity to which the group is bonded.

Accordingly, included within the compounds of the present invention are the tautomeric forms of the disclosed compounds, isomeric forms including enantiomers, stereoisomers, and diastereoisomers, and the pharmaceutically-acceptable salts thereof. The term "pharmaceutically acceptable salts" embraces salts commonly used to form alkali metal salts and to form addition salts of free acids or free bases. Examples of acids which may be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. Suitable pharmaceutically acceptable salts of the compounds of the present invention include, for example, acid addition salts which may, for example, be formed by mixing a solution of the compound according to the invention with a solution of a pharmaceutically acceptable acid, such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. All of these salts may be prepared by conventional means by reacting, for example, the appropriate acid or base with the corresponding compounds of the present invention.

Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicines, the salts of the compounds of the present invention should be pharmaceutically acceptable salts. Other salts may, however, be useful in the preparation of the compounds according to the invention or of their pharmaceutically acceptable salts.

In addition, embodiments of the invention include hydrates of the compounds of the present invention. The term "hydrate" includes but is not limited to hemihydrate, monohydrate, dihydrate, trihydrate and the like. Hydrates of the compounds of the present invention may be prepared by contacting the compounds with water under suitable conditions to produce the hydrate of choice.

In accordance with an embodiment, the present invention provides a compound of formula I, wherein the one or more X is independently F, Cl or Br.

In accordance with another embodiment, the present invention provides a compound of formula I, wherein the one or more X is F and is in the 2, 3, 4, 5, or 6 positions on the phenyl or aryl ring.

In accordance with a further embodiment, the present invention provides a compound of formula I, wherein F is on the 4 or 5 position on the phenyl or aryl ring.

In accordance with an embodiment, the present invention provides a compound of formula I, wherein the Alk group is a $C_1$-$C_3$ alkyl, $C_1$-$C_3$ alkenyl, $C_1$-$C_3$ alkynyl group which may be substituted. In a preferred embodiment, the Alk group is a methyl group.

In accordance with an embodiment, the present invention provides a compound of formula I, wherein $R_1$ is selected from the group consisting of H, $CH_3$ and $NH_2$.

In accordance with an embodiment, the present invention provides a compound of formula I, wherein $R_2$ is $CH_2OH$ or $CONH_2$.

In accordance with an embodiment, the present invention provides a compound of formula I, wherein the compounds are selected from the group consisting of:

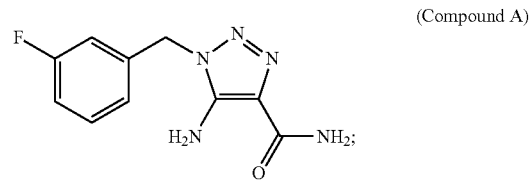
(Compound A)

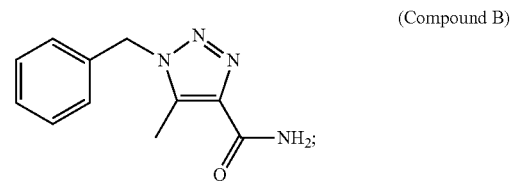
(Compound B)

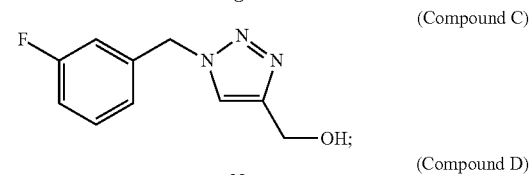
(Compound C)

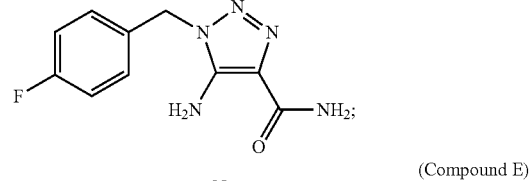
(Compound D)

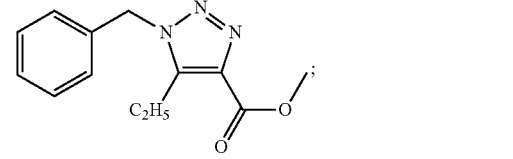
(Compound E)

(Compound F)
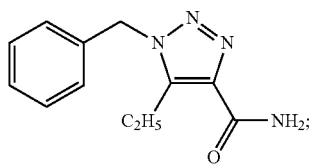

(Compound G)
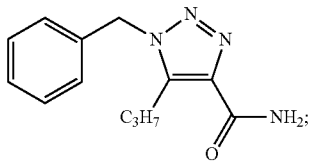

(Compound H)
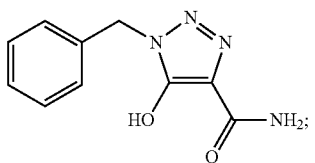

(Compound I)
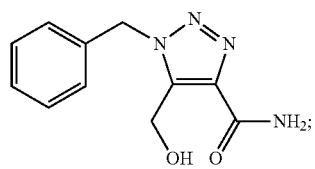

(Compound J)
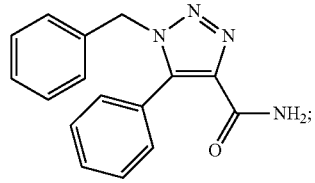

(Compound K)
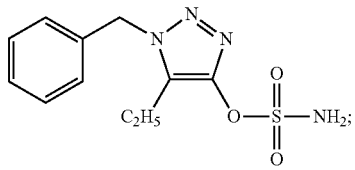

(Compound L)
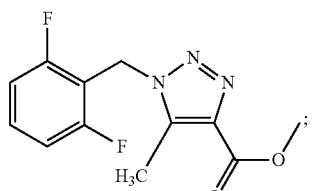

(Compound M)
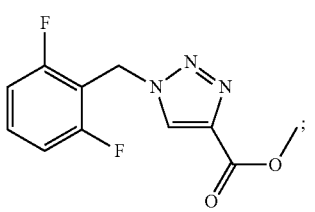

(Compound N)
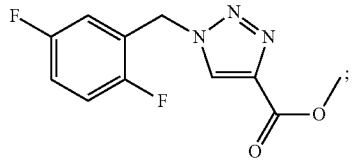

(Compound O)
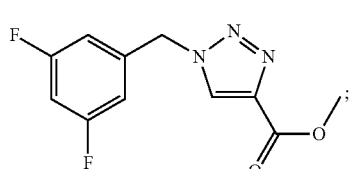

(Compound P)
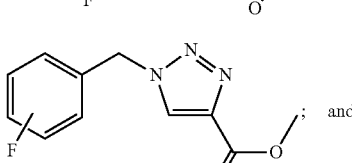

and (Compound Q)
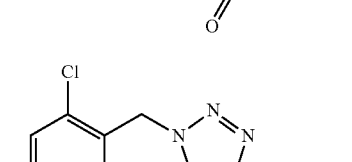

or a salt, solvate, or stereoisomer thereof.

As disclosed herein, some of the compounds are specific for inhibition of activation of the hNav1.1 sodium channel in neurons.

In accordance with an embodiment, the present invention provides a compound of formula I, wherein the compounds are selected from the group consisting of:

(Compound A)
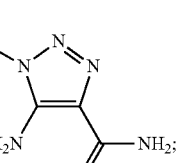

(Compound B)
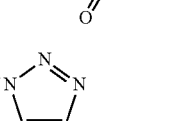

(Compound C)
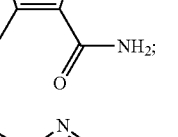

(Compound D)
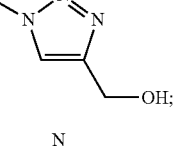

-continued

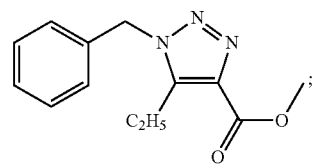
(Compound E)

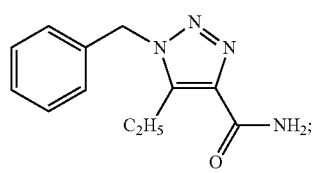
(Compound F)

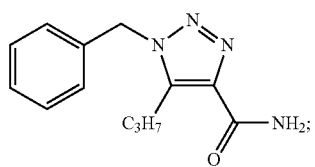
(Compound G)

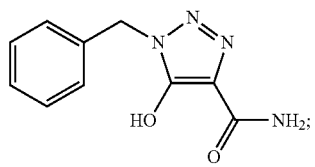
(Compound H)

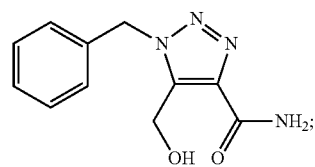
(Compound I)

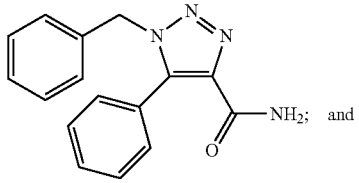
(Compound J)

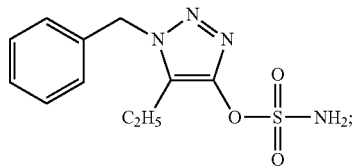
(Compound K)

or a salt, solvate, or stereoisomer thereof.

As disclosed herein, some of the compounds are specific for inhibition of activation of the hNav1.6 sodium channel in neurons.

In accordance with an embodiment, the present invention provides a compound of formula I, wherein the compounds are selected from the group consisting of:

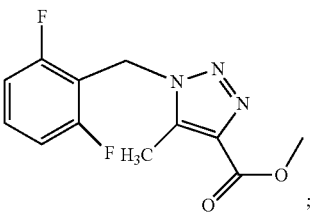
(Compound L)

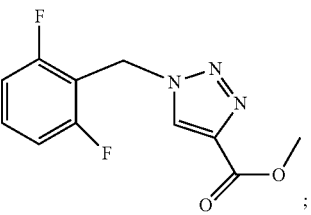
(Compound M)

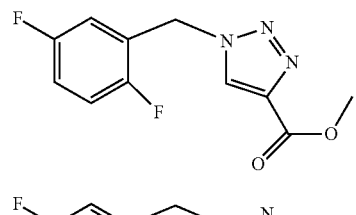
(Compound N)

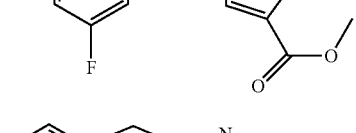
(Compound O)

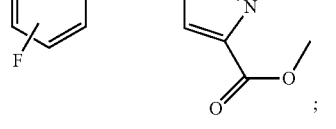
(Compound P)

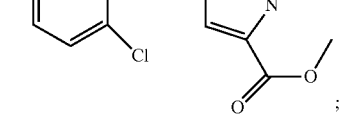
; and

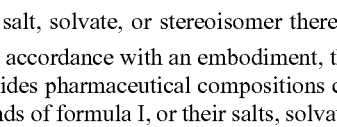
(Compound Q)

or a salt, solvate, or stereoisomer thereof.

In accordance with an embodiment, the present invention provides pharmaceutical compositions comprising the compounds of formula I, or their salts, solvates, or stereoisomers thereof, and a pharmaceutically acceptable carrier.

Embodiments of the invention also include a process for preparing pharmaceutical products comprising the compounds. The term "pharmaceutical product" means a composition suitable for pharmaceutical use (pharmaceutical composition), as defined herein. Pharmaceutical compositions formulated for particular applications comprising the compounds of the present invention are also part of this invention, and are to be considered an embodiment thereof.

In accordance with an embodiment, the present invention provides a pharmaceutical composition comprising a compound of formula I:

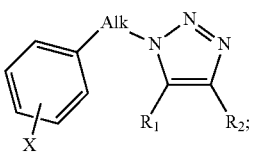

(I)

or a salt, solvate, or stereoisomer thereof, wherein X is H, or one or more electron withdrawing groups such as a halogen, $NH_2$, $NO_2$, $SO_2$, CN, or a $C_1$-$C_6$ alkyl group; Alk is $C_1$-$C_3$ alkyl; $R_1$ is H, $C_1$-$C_6$ alkyl, which may be substituted with OH, $NH_2$, alkylamino, amido, acyl, sulfonyl, sulfonylamino, and cyano groups; and $R_2$, is $C_1$-$C_6$ alkyl, alkenyl, and phenyl, which may be substituted with one or more OH, $NH_2$, alkylamino, amido, acyl, carboxyl, methoxyl, sulfonyl, and cyano groups, and a pharmaceutically acceptable carrier, in an effective amount, for use as a medicament, preferably for use in inhibiting the activation of one or more voltage-gated sodium hNav1.1 or hNav1.6 channels in one or more neurons of a subject, or for use in treating an neurological disorder in a subject.

In accordance with another embodiment, the present invention provides a pharmaceutical composition comprising at least one of the compounds selected from the group consisting of:

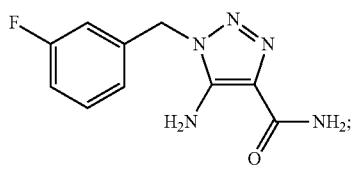
(Compound A)

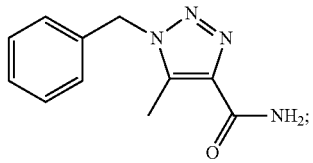
(Compound B)

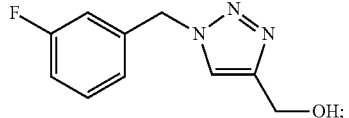
(Compound C)

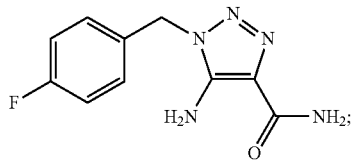
(Compound D)

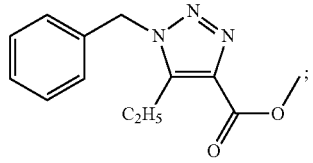
(Compound E)

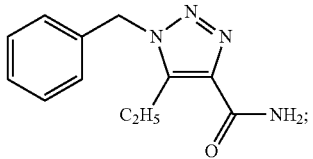
(Compound F)

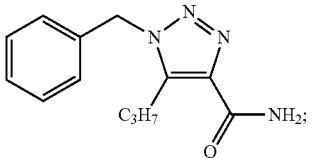
(Compound G)

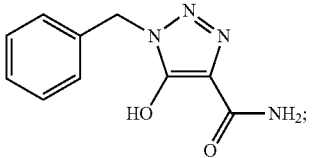
(Compound H)

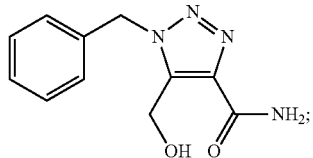
(Compound I)

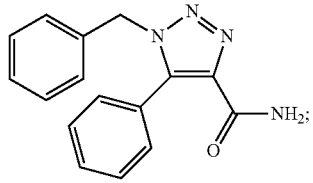
(Compound J)

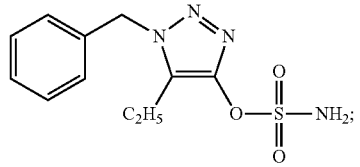
(Compound K)

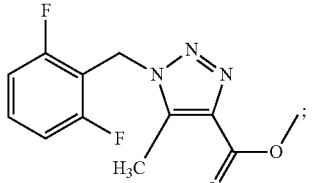
(Compound L)

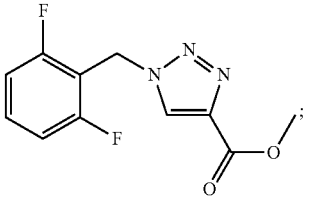
(Compound M)

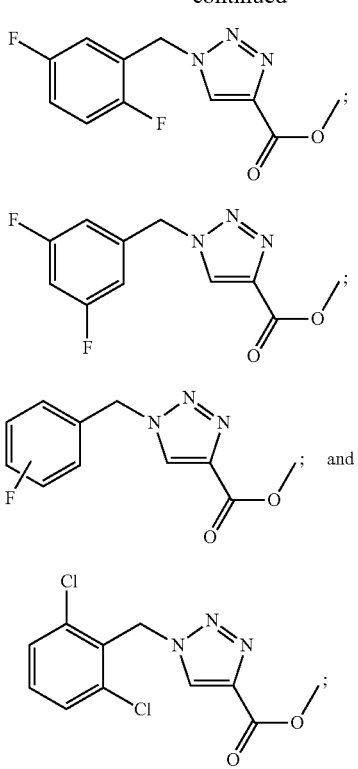

(Compound N); (Compound O); (Compound P); and (Compound Q)

or a salt, solvate, or stereoisomer thereof, and a pharmaceutically acceptable carrier, in an effective amount, for use as a medicament, preferably for use in inhibition of the activation of one or more voltage-gated sodium hNav1.1 or hNav1.6 channels in one or more neurons of a subject, or for use in treating a neurological disorder in a subject.

As used herein, the term "neurological disorder" includes any disease or condition which involves the modulation of activation of voltage-gated sodium hNav1.1 or hNav1.6 channels in one or more neurons in a subject. Such disorders include, but are not limited to, seizures and seizure disorders, including Lennox-Gastaut Syndrome, Dravet syndrome, epileptic encephalopathies, autism, Familial hemiplegic migraine (FHM), anxiety disorders, including Post-traumatic stress disorder (PTSD), panic disorder and obsessive-compulsive disorder, neuropathic pain, and Rett syndrome.

With respect to pharmaceutical compositions described herein, the pharmaceutically acceptable carrier can be any of those conventionally used, and is limited only by physico-chemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. Examples of the pharmaceutically acceptable carriers include soluble carriers such as known buffers which can be physiologically acceptable (e.g., phosphate buffer) as well as solid compositions such as solid-state carriers or latex beads. It is preferred that the pharmaceutically acceptable carrier be one which is chemically inert to the active agent(s), and one which has little or no detrimental side effects or toxicity under the conditions of use.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, suspensions, emulsions or oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

In addition, in an embodiment, the compounds of the present invention may further comprise, for example, binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sorbitan esters, stearic acids), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

The choice of carrier will be determined, in part, by the particular compound, as well as by the particular method used to administer the compound. Accordingly, there are a variety of suitable formulations of the pharmaceutical composition of the invention. The following formulations for parenteral, subcutaneous, intravenous, intramuscular, intraarterial, intrathecal and interperitoneal administration are exemplary, and are in no way limiting. More than one route can be used to administer the compounds, and in certain instances, a particular route can provide a more immediate and more effective response than another route.

Suitable soaps for use in parenteral formulations include, for example, fatty alkali metal, ammonium, and triethanolamine salts, and suitable detergents include, for example, (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the compounds in solution. Preservatives and buffers may be used. In order to minimize or eliminate irritation at the site of injection, such compositions may contain one or more nonionic surfactants, for example, having a hydrophile-lipophile balance (HLB) of from about 12 to about 17. The quantity of surfactant in such formulations will typically range from about 5% to about 15% by weight. Suitable surfactants include, for example, polyethylene glycol sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Injectable formulations are in accordance with the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

For purposes of the invention, the amount or dose of the compounds, salts, solvates, or stereoisomers of any one the compounds of Formula I, as set forth above, administered should be sufficient to effect, e.g., a therapeutic or prophylactic response, in the subject over a reasonable time frame. The dose will be determined by the efficacy of the particular compound and the condition of a human, as well as the body weight of a human to be treated.

In accordance with an embodiment, the present invention provides the use of the compounds or the pharmaceutical compositions disclosed herein in an amount effective for inhibition of the activation of one or more voltage-gated sodium hNav1.1 or hNav1.6 channels in one or more neurons of a subject. In an alternative embodiment, the use includes at least one additional therapeutic agent.

In accordance with an embodiment, the present invention provides the use of the compounds or the pharmaceutical compositions disclosed herein in an amount effective for treating an neurological disorder in a subject. In an alternative embodiment, the use includes at least one additional therapeutic agent. In some embodiments, the neurological disorder is epilepsy or related seizure disorder.

In accordance with an embodiment, the present invention provides the use of the compounds or the pharmaceutical compositions disclosed herein in an amount effective for treating seizure in a subject. In an alternative embodiment, the use includes at least one additional therapeutic agent.

The dose of the compounds, salts, solvates, or stereoisomers of any one the compounds of Formula I, as set forth above, of the present invention also will be determined by the existence, nature and extent of any adverse side effects that might accompany the administration of a particular compound. Typically, an attending physician will decide the dosage of the compound with which to treat each individual patient, taking into consideration a variety of factors, such as age, body weight, general health, diet, sex, compound to be administered, route of administration, and the severity of the condition being treated. By way of example, and not intending to limit the invention, the dose of the compound can be about 0.001 to about 1000 mg/kg body weight of the subject being treated/day, from about 0.01 to about 100 mg/kg body weight/day, or from about 1 mg to about 100 mg/kg body weight/day.

Alternatively, the compounds of the present invention can be modified into a depot form, such that the manner in which the compound is released into the body to which it is administered is controlled with respect to time and location within the body (see, for example, U.S. Pat. No. 4,450,150). Depot forms of compounds can be, for example, an implantable composition comprising the compound and a porous or non-porous material, such as a polymer, wherein the compound is encapsulated by or diffused throughout the material and/or degradation of the non-porous material. The depot is then implanted into the desired location within the body and the compounds are released from the implant at a predetermined rate.

In one embodiment, the compounds of the present invention provided herein can be controlled release compositions, i.e., compositions in which the one or more compounds are released over a period of time after administration. Controlled or sustained release compositions include formulation in lipophilic depots (e.g., fatty acids, waxes, oils). In another embodiment the composition is an immediate release composition, i.e., a composition in which all, or substantially all of the compound, is released immediately after administration.

In yet another embodiment, the compounds of the present invention can be delivered in a controlled release system. For example, the agent may be administered using intravenous infusion, an implantable osmotic pump, a transdermal patch, or other modes of administration. In an embodiment, a pump may be used. In one embodiment, polymeric materials can be used. In yet another embodiment, a controlled release system can be placed in proximity to the therapeutic target, i.e., the brain, thus requiring only a fraction of the systemic dose (see, e.g., *Design of Controlled Release Drug Delivery Systems*, Xiaoling Li and Bhaskara R. Jasti eds. (McGraw-Hill, 2006)).

The compounds included in the pharmaceutical compositions of the present invention may also include incorporation of the active ingredients into or onto particulate preparations of polymeric compounds such as polylactic acid, polglycolic acid, hydrogels, etc., or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

In accordance with the present invention, the compounds of the present invention may be modified by, for example, the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection, than do the corresponding unmodified compounds. Such modifications may also increase the compounds' solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently, or in lower doses than with the unmodified compound.

In accordance with an embodiment, the present invention provides a pharmaceutical composition comprising the compounds of formula I, or salts, solvates, or stereoisomers thereof, and at least one additional therapeutic agent, in an effective amount, and a pharmaceutically acceptable carrier.

As used herein, the term "additional therapeutic agent" means one or more active agents that are used in the treatment of epileptic diseases and seizure disorders. Examples of such active agents include, but are not limited to, anticonvulsants, such as carbamazepine, gabapentin, lamotrigine, phenytoin, valproic acid, topiramate, felbamate, and clobazam. Other therapeutic agents useful in combination with the inventive compounds and compositions described herein include neurological agents, such as, barbiturate anticonvulsants, such as phenobarbital and primidone; benzodiazepine anticonvulsants, such as clonazepam, diazepam, and lorazepam; anti-agents, such as bromocriptine, levodopa, carbidopa, and pergolide; benzodiazepine anticonvulsants, anti-migraine agents, anti-parkinsonian agents, anti-vertigo agents, opiate agonists, and opiate antagonists, psychotropic agents, such as antidepressants, heterocyclic antidepressants, monoamine oxidase inhibitors selective serotonin re-uptake inhibitors tricyclic antidepressants, antimanics, anti-psychotics, such as clozapine, haloperidol, and risperidone; phenothiazine antipsychotics, anxiolytics, sedatives, and hypnotics, barbiturate sedatives and hypnotics, benzodiazepine anxiolytics, sedatives, and hypnotics such as clonazepam, diazepam, lorazepam, oxazepam, and prazepam, and psychostimulants such as methylphenidate and pemoline.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

As used herein, the term "modulate" means that the compounds of formula I, described herein either increase or decrease the activity of the one or more voltage-gated sodium (Nav) channels in one or more neurons of a subject. In a preferred embodiment, the compounds of formula I described herein inhibit the activation of the hNav channels, particularly hNav1.1 and hNav1.6. In a preferred embodiment, the inventive compounds inhibit the activation of one or more voltage-gated sodium hNav1.1 and hNav1.6 channels in the neurons of a subject.

In accordance with an embodiment, the present invention provides a method for treating an epilepsy disorder in a subject comprising administering to the subject a therapeutically effective amount of the compound of formula I, or compositions comprising them.

As used herein, the term "epilepsy disorder" refers to any of a number of diseases that are characterized by a neurological condition that makes people susceptible to seizures. A seizure is a change in sensation, awareness, or behavior brought about by a brief electrical disturbance in the brain. Seizures vary from a momentary disruption of the senses, to short periods of unconsciousness or staring spells, to convulsions. Some people have just one type of seizure. Others have more than one type.

In accordance with an embodiment, the present invention provides a method for treating a seizure in a subject comprising administering to the subject a therapeutically effective amount of the compound compounds of formula I described herein or compositions comprising them.

Without being limited to any particular theory of action, it will be understood by those of ordinary skill in the art that the compounds of formula I described herein or compositions comprising them have anti-convulsant properties due to their modulatory activity of hNav1.1 or hNav1.6 sodium channels.

As used herein, the term "treat," as well as words stemming therefrom, includes preventative as well as disorder remitative treatment. The terms "reduce," "suppress," "prevent," and "inhibit," as well as words stemming therefrom, have their commonly understood meaning of lessening or decreasing. These words do not necessarily imply 100% or complete treatment, reduction, suppression, or inhibition.

Compounds for Use in the Inhibition of Activation of hNav1.1 Sodium Channels.

Given their unique role in electrical signaling and subsequent implications in various epilepsy disorders, voltage-gated sodium (Nav) channels within the central nervous system (CNS) are influenced by anti-epileptic drugs (AEDs). Of the nine Nav channel isoforms (Nav1.1-Nav1.9) identified in humans, four are expressed predominantly in the CNS (Nav1.1 (SCN1A), Nav1.2 (SCN2A), Nav1.3 (SCN3A), and Nav1.6 (SCN8A)). Supporting their physiological importance, mutations in Nav1.1 (more than 1200), Nav1.2, and Nav1.6 have been linked to various epilepsy phenotypes whereas Nav1.3 is believed to also be involved in nociception after channel upregulation due to spinal cord injury. To test whether the compounds of the present invention specifically influence hNav1.1, we transiently expressed human (h)Nav1.1, hNav1.2, hNav1.3, and hNav1.6 in a robust heterologous expression system and found that a clinically relevant concentration of our lead compound (Compound F) primarily influences the voltage-dependence of hNav1.1 activation. Subsequent experiments with structurally related compounds reveal that chemical derivatization at particular positions on the triazole pharmacophore may be exploited to obtain specific inhibition of hNav1.1 activation.

Clinical Applications:

The results presented here together with previously reported observations suggest that our new compounds have the potential to primarily target the hNav1.1 isoform in the brain. As a result, these compounds can find use as a therapeutic in the following diseases.

Seizures

Since anomalous hNav1.1 behavior (molgen.vib-ua.be/scn1amutations/) has been implicated in Lennox-Gastaut Syndrome as well as partial or refractory focal seizures, the expected therapeutic effects of Compound F may indeed stem from its ability to shift the voltage-dependence of activation of hNav1.1 channels to more positive potentials (FIG. 15), a notion worth exploring for treating seizure disorders involving hNav1.1 gain-of-function mutations such as GEFS+. However, rufinamide may be contraindicated with patients in whom Nav1.1 function is already impaired. For instance, Nav1.1 deletion in mouse hippocampal and cortical interneurons decreases sustained high-frequency firing of action potentials by reducing overall sodium current without altering its voltage-dependent features. Subsequently, loss ofNav1.1 function may lead to hyperexcitability and epileptic seizures in patients with Dravet syndrome and autism. Consistent with the protection achieved in wild-type mice, our Compound B and related novel compounds may also find use as a general anticonvulsant.

Thus, in accordance with one or more embodiments, the present invention provides methods for prevention or treatment of seizures and seizure disorders in a subject by administering to the subject an effective amount of a compound of formula I, or a pharmaceutical composition comprising a compound of formula I and a pharmaceutically acceptable carrier, with, or without an additional therapeutic agent.

Migraine

Familial hemiplegic migraine (FHM) is a rare monogenic subtype of migraine with aura, characterized by motor auras. Although the majority of FHM families have mutations in the CACNA1A and ATP1A2 genes, a recent discovery is that ~5% of FHM families are explained by mutations in the SCN1A gene. For example, FHM patients in two studied families had pure hemiplegic migraine with highly variable severity and frequency of attacks. Researchers identified a novel SCN1A missense mutation p.Ile1498Met in all three tested hemiplegic migraine patients of one family. In the other family, a novel SCN1A missense mutation p.Phe1661Leu was identified in six out of eight tested hemiplegic migraine patients. Both mutations affect amino acid residues that either reside in an important functional domain (in the case of Ile(1498)) or are known to be important for kinetic properties of the NaV 1.1 channel (in the case of Phe(1661)). Moreover, another recent study identified a T1174S Nav1.1 mutation in a three-generation family with both epileptic and FHM phenotypes. Functional effects were divergent: positive shift of the activation curve and deceleration of recovery from fast inactivation, consistent with loss of function, and increase of persistent current (I(NaP)), consistent with gain of function. As shown by a computational model, T1174S could in some conditions induce overall loss of function, and in others gain of function; Q 1489K induced gain of function in all the conditions. As such, Nav1.1 has become a drug target for FHM and the compounds of the present invention could be very useful therapeutics for migraine and related disorders.

Thus, in accordance with one or more embodiments, the present invention provides methods for prevention or treatment of migraine and migraine related disorders in a subject by administering to the subject an effective amount of a compound of formula I, or a pharmaceutical composition comprising a compound of formula I and a pharmaceutically acceptable carrier, with, or without an additional therapeutic agent.

Post-Traumatic Stress Disorder

Anxiety disorders are commonly occurring disorders of psychiatric illnesses with a vast economic burden. In addition to generalized anxiety disorder, they encompass post-traumatic stress disorder (PTSD), panic disorder, obsessive compulsive disorder and social as well as other phobias. Post-traumatic stress disorder can be severe and chronic, with some studies suggesting a lifetime prevalence of 2% to 8% in the general world-wide population. Post-traumatic stress disorder typically follows a psychologically distressing traumatic event. These events may include military combat, physical assault, motor vehicle accidents, and natural disasters. The response to the event can involve intense fear or a feeling of helplessness. Most people recover from the traumatic event with time and return to normal life. In contrast, in post-traumatic stress disorder victims, symptoms persist and may worsen with time, preventing a return to normal life. Psychotherapy is currently the backbone of post-traumatic disorder treatment. Medication can enhance the effectiveness of psychotherapy. However, selective serotonin reuptake inhibitors (SSRIs) are the only medications approved for treating PTSD by the FDA. Many unwanted side effects and characteristics are associated with SSRI usage. As such, there is a need for the development of treatments for post-traumatic stress disorder that are safe and effective. AEDs such as phenytoin and rufinamide show promise in treating anxiety disorders, possibly through a mechanism related to altering Nav1.1 function. For example, one study revolved around a patient with bipolar disorder and multiple psychiatric and medical comorbidities (panic disorder, alcohol abuse, chronic pain) that also had been extraordinarily refractory to treatment and had failed countless pharmacological and non-pharmacological treatment attempts. In the context of an acute worsening of patient condition, rufinamide 400 mg 1 tablet twice daily was added to the pharmacological regimen, leading to a very rapid (within days) clinical improvement. The patient reported a marked improvement in depressive and anxiety symptoms, significant mood stabilization and reduction in mood swings, and a reduction in craving for alcohol and binge eating. This case as well as shows the potent therapeutic effects of the Nav1.1-targeting molecules with respect to bipolar disorder, depressive and anxiety disorders, panic disorder and obsessive-compulsive disorder. Moreover, the US Army proposes to treat PTSD with rufinamide. They also suggest methods of treating kindling and improving resilience with rufinamide. Moreover, they provide insights into diagnosing PTSD in a patient by administering to the patient a therapeutically effective amount of rufinamide and assessing at least one of sign, symptom, or symptom cluster of post-traumatic stress disorder; and diagnosing post-traumatic stress disorder in the patient if the rufinamide reduces at least one of sign, symptom, and symptom cluster of post-traumatic stress disorder. Together with our data on rufinamide and the compounds of the present invention, this information clearly points to an important role for Nav1.1 in anxiety-related disorders such as PTSD and their treatment by using Nav1.1 targeting drugs.

Thus, in accordance with one or more embodiments, the present invention provides methods for prevention or treatment of anxiety and anxiety related disorders in a subject by administering to the subject an effective amount of a compound of formula I, or a pharmaceutical composition comprising a compound of formula I and a pharmaceutically acceptable carrier, with, or without an additional therapeutic agent.

Neuropathic Pain

Neuropathic pain refers to pain that originates from pathology of the nervous system. Diabetes, infection (herpes zoster), nerve compression, nerve trauma, "channelopathies," and autoimmune disease are examples of diseases that may cause neuropathic pain. The development of both animal models and newer pharmacological strategies has led to an explosion of interest in the underlying mechanisms. Neuropathic pain reflects both peripheral and central sensitization mechanisms. Abnormal signals arise not only from injured axons but also from the intact nociceptors that share the innervation territory of the injured nerve. The present inventors have discovered that Nav1.1 is expressed in pain-sensing neurons in the periphery and as such, has become a target for therapeutics designed to alleviate pain. It may also explain why off-label use of AEDs is sometimes effective in patients with severe types of (neuropathic) pain, an observation that still puzzles clinicians. For example, in an effort to find drugs for neuropathic pain, researchers uncovered that rufinamide stabilizes the inactivated state of the Nav1.7 isoform which is typically found in the peripheral nervous system. However, this effect is rather small compared to that on hNav1.1 activation voltage, and at the time that study was published, it was not known that Nav1.1 is also expressed in the peripheral nervous system.

Thus, in accordance with one or more embodiments, the present invention provides methods for prevention or treatment of pain and pain related disorders in a subject by administering to the subject an effective amount of a compound of formula I, or a pharmaceutical composition comprising a compound of formula I and a pharmaceutically acceptable carrier, with, or without an additional therapeutic agent.

Compounds for Use in the Inhibition of Activation of hNav1.6 Sodium Channels.

Of the nine Nav channel isoforms (Nav1.1-Nav1.9) identified in humans, four are expressed predominantly in the CNS (Nav1.1 (SCN1A), Nav1.2 (SCN2A), Nav1.3 (SCN3A), and Nav1.6 (SCN8A)) of which Nav1.6 is primarily expressed in nodes of Ranvier. Supporting their physiological importance, mutations in Nav1.1, Nav1.2, and Nav1.6 have been linked to various epilepsy phenotypes whereas Nav1.3 is believed to also be involved in nociception after channel upregulation due to spinal cord injury. To test whether the inventive compounds primarily influence hNav1.6, we transiently expressed human (h)Nav1.1, hNav1.2, hNav1.3, and hNav1.6 in a robust heterologous expression system and found that a clinically relevant concentration of our lead compound (see above) primarily influences the hNav1.6 channel availability (or steady-state inactivation) activation. Subsequent experiments with structurally related compounds reveal that chemical derivatization at particular positions on the triazole pharmacophore may be exploited to specific inhibition of hNav1.6.

EXAMPLES

Channel constructs. Human (h)Nav1.1, Nav1.2, Nav1.3, Nav1.6, and $\beta_1$ (NCBI reference: NM_001037) clones were obtained from OriGene Technologies, Inc. (USA) and modified for expression in *Xenopus* oocytes. To check for undesired re-arrangement events, the DNA sequence of all constructs was confirmed by automated DNA sequencing before further usage. cRNA was synthesized using T7 polymerase (mMessage mMachine kit, Life Technologies) after linearizing the DNA with appropriate restriction enzymes.

Two-electrode voltage-clamp recording from *Xenopus* oocytes. Channels were expressed in *Xenopus* oocytes together with $\beta_1$ in a 1:5 molar ratio and currents were studied following 1-2 days incubation after cRNA injection (incubated at 17° C. in 96 mM NaCl, 2 mM KCl, 5 mM HEPES, 1 mM $MgCl_2$ and 1.8 mM $CaCl_2$, 50 µg/ml gentamycin, pH 7.6 with NaOH) using two-electrode voltage-clamp recording techniques (OC-725C, Warner Instruments) with a 150 µl recording chamber. Data were filtered at 4 kHz and digitized at 20 kHz using pClamp software (Molecular Devices). Microelectrode resistances were 0.1-1 MΩ when filled with 3 µM KCl. The external recording solution contained 100 mM NaCl, 5 mM HEPES, 1 mM $MgCl_2$ and 1.8 mM $CaCl_2$, pH 7.6 with NaOH. All experiments were performed at room temperature (~22° C.). Leak and background conductances, identified by blocking the channels with tetrodotoxin, were subtracted for all of the Nav channel currents. Chemicals were obtained from Sigma, Vitasmlabs, and Maybridge (through eMolecules).

Analysis of channel activity and drug-channel interactions. Voltage-activation relationships were obtained by measuring steady-state currents and calculating conductance (G), and a single Boltzmann function was fitted to the data according to: $G/G_{max} = (1 + e^{-zF(V-V_{1/2})/RT})^{-1}$ where $G/G_{max}$ is the normalized conductance, z is the equivalent charge, $V_{1/2}$ is the half-activation voltage, F is Faraday's constant, R is the gas constant and T is temperature in Kelvin. Rufinamide and derivatives were dissolved in DMSO (stock solution) and ad hoc diluted to 100 µM working concentration while taking great care not to reach the maximal solubility of the compounds. *Xenopus* oocytes expressing the various Nav channel isoforms were incubated in solutions containing 100 µM drug (final DMSO concentration was 1% or less) for at least one hour. No significant difference was observed in drug-induced effects on Nav channels between one hour and overnight incubation. Differences in reported values were only considered significant when p<0.005 (Student's t-test). Off-line data analysis and statistics were performed using Clampfit (Molecular Devices), Excel (Microsoft Office) and Origin 7.5 (Originlab).

Action potential threshold recordings in hippocampal neurons. Hippocampal neurons were dissected from Sprague Dawley rat embryos at embryonic day 18. Cells were treated with papain (Worthington Biochemical), dissociated with a pipette and plated over coverslips coated with collagen (Life Technologies) and poly-D-Lysine (Sigma-Aldrich). Astrocyte beds were prepared at a density of 80,000 cells/ml and cultured in DMEM (Life Technologies) with 10% Fetal Bovine Serum, 6 mM glutamine for 14 days in 5% $CO_2$ at 37° C. Total medium was changed every week. Neurons were plated over confluent astrocyte beds at a density of 150,000 cells/ml and cultured for 3 weeks in Neurobasal media (Life Technologies) supplemented with B27 and 2 mM glutaMAX. Half of the media was changed every 3-4 days. Cells were treated for 3 hours with compound B in 0.3% DMSO or control (media containing 0.3% DMSO) before recording. Coverslips were transferred to a chamber perfused at 2 ml/minute at 32° C. with ACSF containing (in mM): 140 NaCl, 5 KCl, 2 $CaCl_2$, 2 $MgCl_2$, 10 HEPES, and 10 Glucose (pH 7.3 adjusted with NaOH). An Axopatch 200B equipped with a Digidata 1440 digitizer and pClamp 10 software were used. Whole-cell current clamp recordings were performed using borosilicate glass pipettes (4-6 MΩ) filled with a solution containing (in mM): 135 K-gluconate, 20 KCl, 10 HEPES, 4 Mg-ATP, 0.3 $Na_2GTP$, 0.5 EGTA. Action potential thresholds were measured by a series of 100 ms, 10 pA depolarizing current injections. At the minimal current injection needed to elicit an action potential, firing threshold was determined by calculating the potential at which the rate of rise crossed 40V/s, using AxoGraph X software. Data are presented as mean±s.e.m. Statistical analysis using the Student's t-test was performed using GraphPad Prism 6. The Johns Hopkins University Institutional Animal Care and Use Committee approved all experimental protocols involving rats.

Animal husbandry and drug administration. Male Crl: CF1 mice (10-12 weeks old, Charles River) were housed under a 12 hour light-dark cycle with free access to food and water and all experiments were carried out between 10 am and 4 pm. 1-[phenyl-methyl]-1H-1,2,3-triazole-4-carboxamide-5-methyl (Compound B) (Sigma Aldrich) was suspended in a 40% solution of cyclodextrin (Sigma Aldrich) in sterile saline (0.9%) and 15 minutes prior to each seizure induction paradigm, 75 mg/kg of compound B was administered via intraperitoneal injection (ip) injection. Vehicle treated animals were similarly administered 40% cyclodextrin and served as the controls for each experiment. The Emory University Institutional Animal Care and Use Committee approved all experimental protocols involving mice.

Seizure induction paradigms and analyses. Picrotoxin seizure induction—15 minutes prior to i.p. injection of picrotoxin (10 mg/kg, Sigma Aldrich), mice were administered vehicle or compound B (n=12 per group). Latencies to the first myoclonic jerk, forelimb clonus, and generalized tonic-clonic seizure were compared between compound B and vehicle-treated mice. The myoclonic jerk is characterized by a sudden jerk of the upper body whereas forelimb clonus involves rapid movement of the forelimbs for at least 5s. Finally, the generalized tonic-clonic seizure involves the loss of postural control with rapid movement of the limbs for at least 5s.

Flurothyl Seizure induction. Latencies to flurothyl-induced seizures were determined as previously described (*Neurobiol Dis* 49C, 211-220 (2012)). Briefly, flurothyl (2,2,2-trifluroethylether; Sigma Aldrich) was dispensed at a rate of 20 μl/minute into a Plexiglas chamber and latencies to three behavioral phenotypes were compared between vehicle-treated and compound B-treated (75 mg/kg) mice (n=12 per group): 1) the first myoclonic jerk, 2) a generalized tonic-clonic seizure, and 3) a generalized tonic-clonic seizure with tonic extension. Similar to picrotoxin-mediated seizure induction, the myoclonic jerk is the first observable behavioral phenotype followed by the generalized tonic-clonic seizure which is characterized by a loss of postural control with rapid movement of all four limbs for at least 5 s. Lastly, the generalized tonic-clonic seizure with tonic hind limb extension involves the loss of postural control and rapid movement of all four limbs followed by downward extension of the limbs parallel to the body.

6 Hz psychomotor seizure induction. Topical anesthetic (0.5% tetracaine hydrochloride ophthalmic solution) was applied to the cornea 30 minutes before testing. Fifteen minutes prior to seizure induction, mice were administrated vehicle or compound B (n=12 per group). Each mouse was manually restrained and corneal stimulation (0.2 ms pulse, 6 Hz, 3s) was performed at a current intensity of 17 mA (ECT Unit 57800; Ugo Basile, Comerio Italy). The mice were observed for behavioral responses immediately following stimulation and seizures were scored based on a modified Racine scale: 0, no behavior; 1, staring; 2, forelimb clonus; 3, rearing and falling. The mice were randomized into two groups and in the first trial one group received the vehicle whereas the other was administered compound B. The second trial was performed one week later with each group receiving the opposite treatment. The resulting data were combined since no statistically significant differences were observed between the two trials.

Statistical analysis. A Student's t-test was used to identify statistically significant differences in latencies between vehicle- and compound B-treated groups for each seizure phenotype following administration of flurothyl and picrotoxin. A Fisher Exact test was applied to determine differences in the percent of vehicle- and compound B-treated mice exhibiting seizures in the 6 Hz seizure induction paradigm, and a Wilcoxon matched-pairs signed rank test determined the differences in seizure severity. All data are presented as the mean±s.e.m.; p values <0.05 were considered significant.

Example 1

Figure 1:
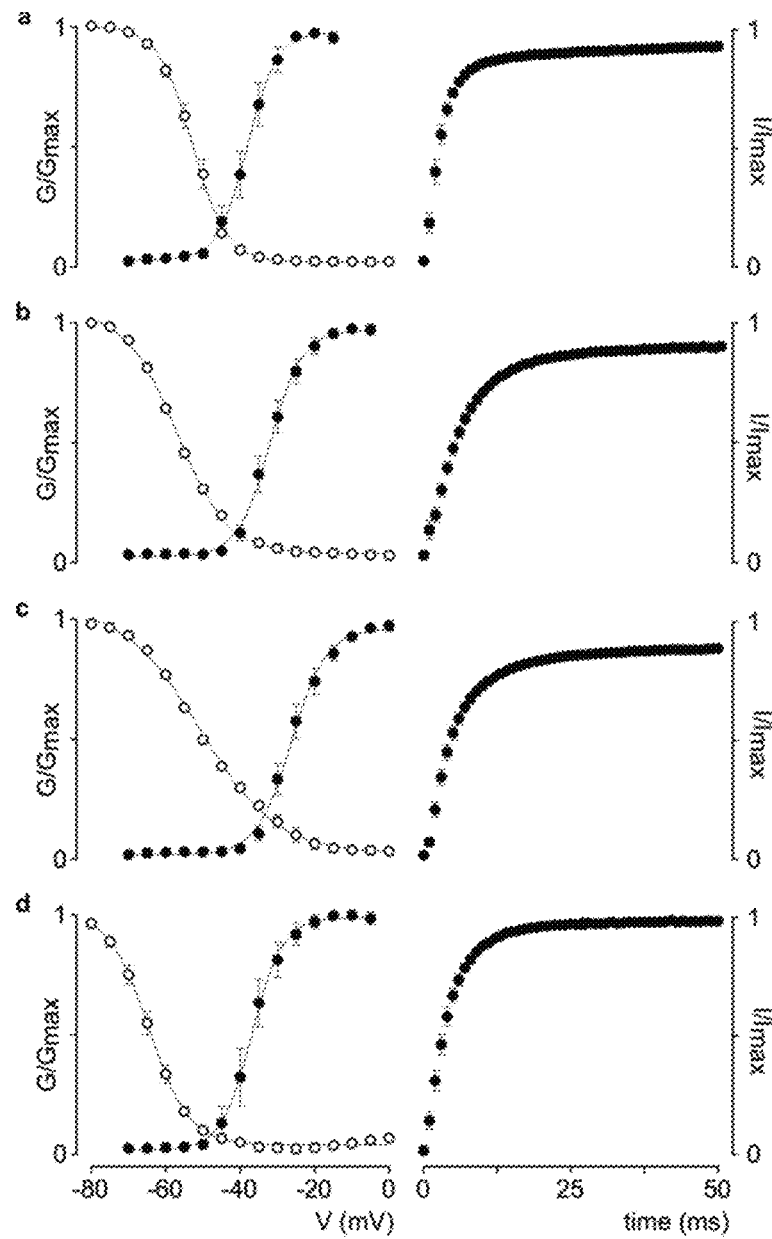
FIG. 1: Gating characteristics of hNav1.1, hNav1.2, hNav1.3, and hNav1.6. Left column shows normalized conductance-voltage (G/Gmax) and steady-state inactivation (I/Imax) relationships whereas right column displays recovery from fast inactivation determined by a double pulse protocol to Gmax with a varying time between pulses (0-50 ms) of hNav1.1 (a), hNav1.2 (b), hNav1.3 (c), and hNav1.6 (d). Curve fitting is described in materials and methods section and values are reported in Table 1. n=5-10 and error bars represent s.e.m.

Expressing human Nav channel isoforms in *Xenopus* oocytes. To identify the molecular target of rufinamide in humans, we wanted to examine potential drug-induced alterations of human Nav channel opening and closing (i.e. gating). Although stable cell lines of human (h)Nav1.1, hNav1.2, hNav1.3, and hNav1.6 have been reported. DNA re-arrangement events and low protein levels have hampered in-depth experiments with these genes in *Xenopus* oocytes, a robust heterologous expression system widely used to address fundamental questions on the gating mechanisms and pharmacological sensitivities of ion channels. By combining DNA transformations into low-copy *E. Coli* variants (CopyCutter EPI400™) with careful full-length clone sequencing, we were able to consistently obtain ionic currents for all four human Nav channel isoforms in *Xenopus* oocytes (FIG. 1). Examination of the G-V relationships for hNav1.1, hNav1.2, hNav1.3, and hNav1.6 (FIG. 1) reveals that the midpoints ($V_{1/2}$) for channel activation are −37.8 mV, −31.4 mV, −25.4 mV, and −36.7 mV, respectively (Table 1). Although the same relative order of midpoints is essentially observed when performing mammalian cell recordings, their absolute values as well as those from channel availability and recovery from inactivation measurements (FIG. 1, Table 1) differ substantially. However, this observation is not surprising considering the variability in lipid membrane and auxiliary subunit composition between diverse cell types. Next, we applied rufinamide to hNav1.1, hNav1.2, hNav1.3, and hNav1.6 and assessed whether this drug alters channel gating.

TABLE 1

Effects of rufinamide and its derivatives on human Nav channel isoforms

|  |  | hNa$_v$1.1 | hNa$_v$1.2 | hNa$_v$1.3 | hNa$_v$1.6 |
|---|---|---|---|---|---|
| Control | Activation ($V_{1/2}$) | −37.8 ± 1.7 mV | −31.4 ± 1.5 mV | −25.4 ± 1.4 mV | −29.0 ± 2.2 mV |
|  | Inactivation ($V_{1/2}$) | −52.9 ± 1.0 mV | −57.1 ± 0.3 mV | −52.2 ± 0.7 mV | −64.8 ± 1.2 mV |
|  | Recovery (T) | 3.4 ± 0.2 ms | 6.6 ± 0.5 ms | 5.6 ± 0.3 ms | 4.4 ± 0.3 ms |
| DMSO | Activation ($V_{1/2}$) | −38.2 ± 1.9 mV | −31.7 ± 1.2 mV | −24.7 ± 1.6 mV | −26.7 ± 1.1 mV |
|  | Inactivation ($V_{1/2}$) | −49.4 ± 0.3 mV | −59.7 ± 0.4 mV | −52.8 ± 0.9 mV | −65.1 ± 0.8 mV |
|  | Recovery (T) | 3.8 ± 0.5 ms | 7.1 ± 0.4 ms | 6.5 ± 0.3 ms | 5.0 ± 0.4 ms |
| Rufinamide | Activation ($V_{1/2}$) | −30.6 ± 0.9 mV** | −29.5 ± 1.2 mV | −24.5 ± 2.4 mV | −28.1 ± 0.8 mV |
|  | Inactivation ($V_{1/2}$) | −47.8 ± 1.6 mV | −57.7 ± 0.5 mV | −52.6 ± 1.6 mV | −60.0 ± 0.7 mV** |
|  | Recovery (T) | 5.1 ± 0.2 ms** | 10.6 ± 0.3 ms** | 9.2 ± 0.5 ms** | 7.4 ± 0.3 ms** |

|  |  | Compound A | Compound B | Compound C | Compound D |
|---|---|---|---|---|---|
| hNa$_v$1.1 | Activation ($V_{1/2}$) | −30.8 ± 1.0 mV** | −27.4 ± 1.0 mV** | −38.4 ± 1.3 mV | −32.5 ± 2.3 mV |
|  | Inactivation ($V_{1/2}$) | −50.5 ± 1.2 mV | −49.4 ± 0.3 mV | −49.2 ± 0.6 mV | −49.8 ± 1.6 mV |
|  | Recovery (T) | 4.1 ± 0.5 ms | 3.9 ± 0.1 ms | 3.1 ± 0.1 ms | 3.9 ± 0.3 ms |

Drug values are compared to DMSO values for statistical comparison which is considered significant if the result of the Student's t-test indicated a p<0.005 (as shown in the table by the double asterisk).

Example 2

Figure 4:
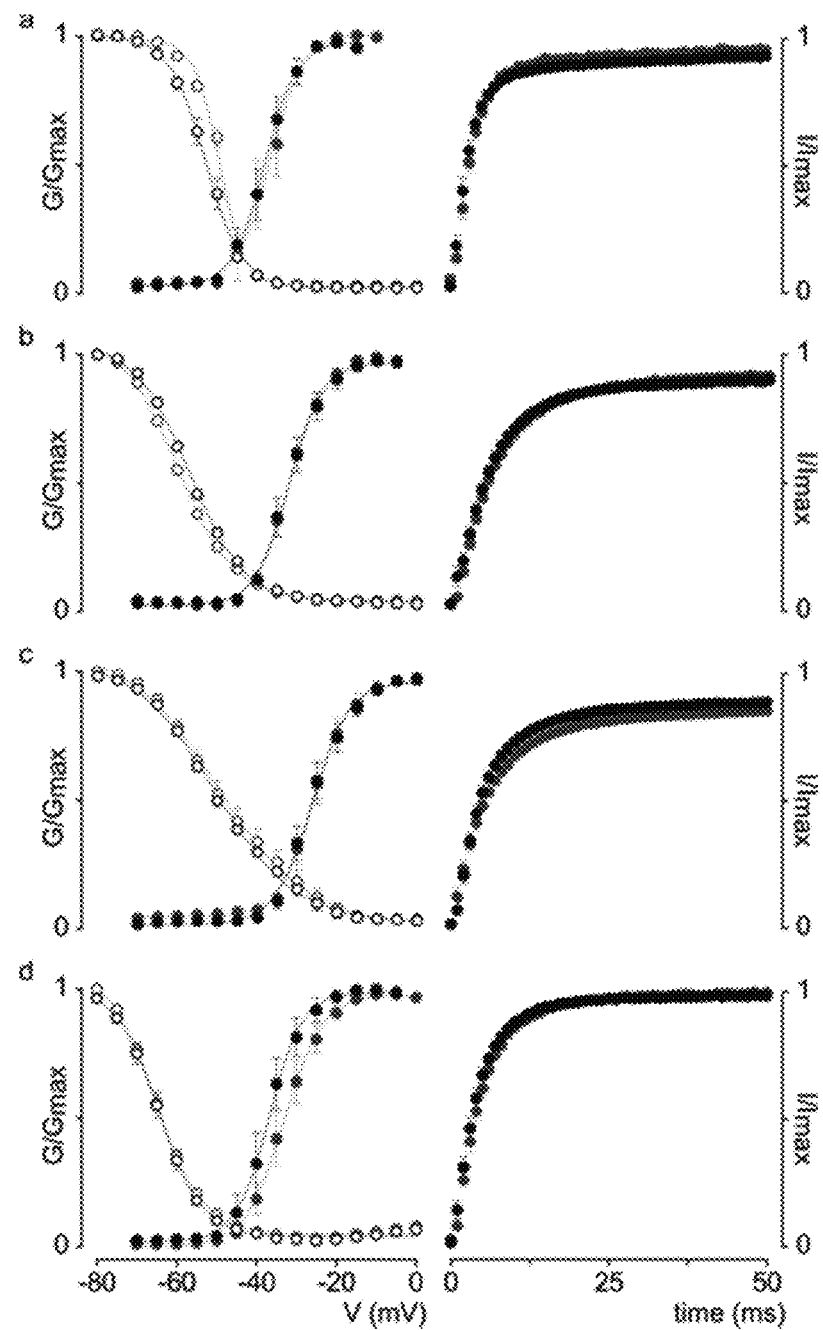
FIG. 4: Effect of DMSO on hNav channel isoforms involved in epilepsy. FIGS. a-d, Left column shows normalized deduced conductance-voltage (G/Gmax) and steady-state inactivation (I/Imax) relationships whereas right column displays recovery from fast inactivation determined by a double pulse protocol to Gmax. All data is shown before (black) and after addition of 1% (v/v) DMSO on hNav1.1 (b), hNav1.2 (c), hNav1.3 (d), and hNav1.6 (e). This concentration of DMSO only influences opening of hNav1.6 rendering the effect of 100 μM rufinamide on this channel not statistically significant; n=5-8 and error bars represent s.e.m.

The gating process of human Nav channels is altered by rufinamide. Rufinamide, or 1-[(2,6-difluorophenyl)methyl]-1H-1,2,3-Triazole-4-carboxamide, is slightly soluble in water but dissolves readily in DMSO at concentrations up to 9 mg/ml (FIG. 2a). As such, patients are given the drug either as a tablet formulation (Banzel®) or an oral suspension (Inovelon®), preferably to be taken with food. Based on these properties, we dissolved rufinamide in DMSO and diluted this stock solution with appropriate recording media to a final concentration of 100 μM, thereby approximating clinically observed serum quantities. As a result of this preparation, Nav channel-expressing oocytes were exposed to 100 μM rufinamide in a solution containing less than 1% DMSO. Control experiments without the drug revealed that the gating properties of hNav1.1, hNav1.2, and hNav1.3 are not affected when exposed to 1% DMSO (FIG. 4, Table 1). However, the G-V relationship of hNav1.6 is shifted to more depolarized potentials (p<0.005; FIG. 1, Table 1) suggesting that this particular Nav channel isoform may be sensitive to DMSO-induced alterations in lipid membrane mechanics. Subsequently, the gating parameters obtained from DMSO-treated Nav channel isoforms are considered to be the control values (Table 1).

Figure 2:
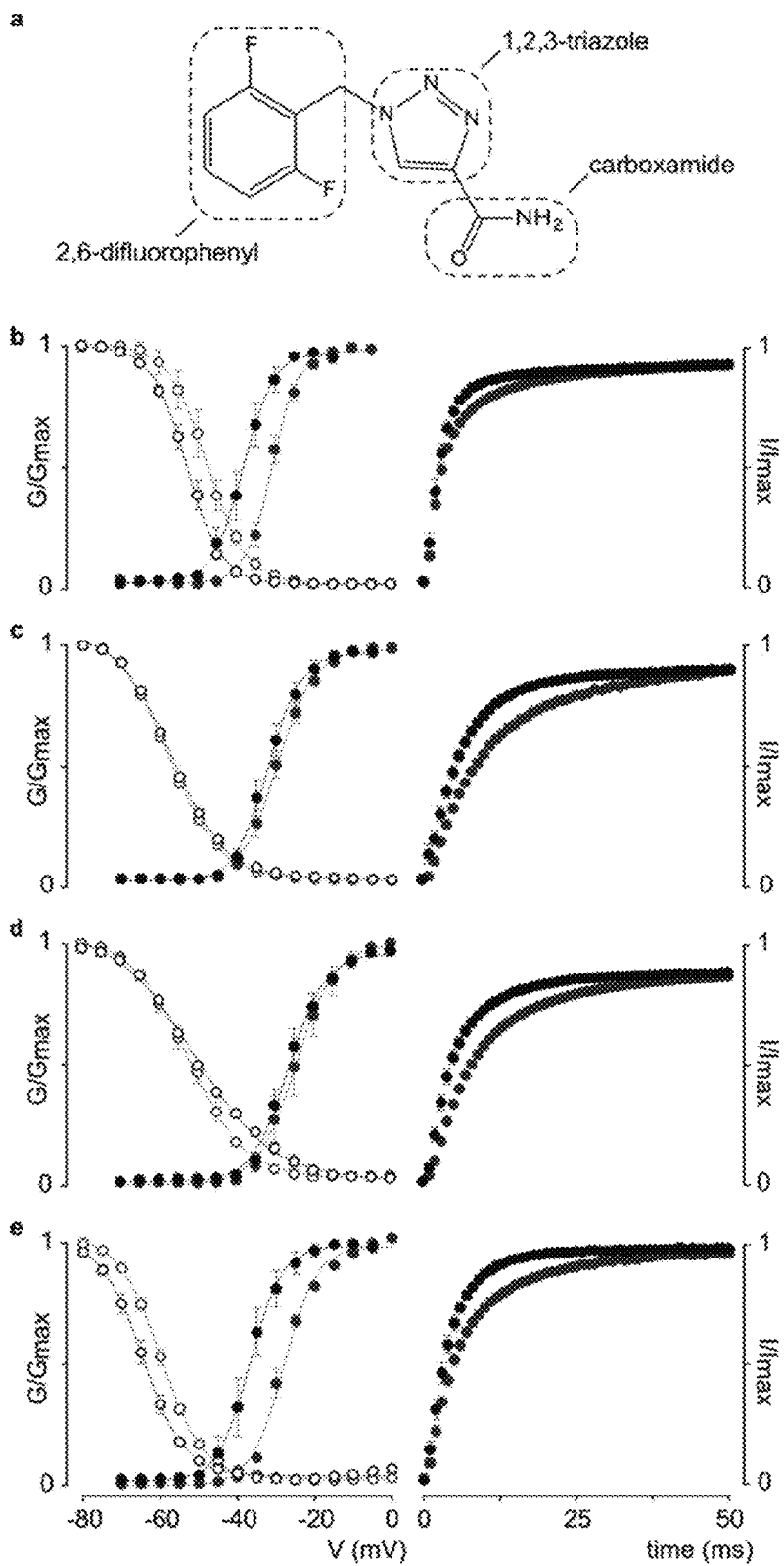
FIG. 2: Effect of rufinamide on human Nav channel isoforms involved in epilepsy a, Molecular organization of rufinamide consisting of the 1,2,3-triazole ring connecting the 2,6-difluorophenyl and the carboximide. b-e, Left column shows normalized deduced conductance-voltage (G/Gmax) and steady-state inactivation (I/Imax) relationships whereas right column displays recovery from fast inactivation determined by a double pulse protocol to Gmax. The figure clearly shows that rufinamide inhibits hNav1.1 opening whereas the effect on hNav1.6 is not significant compared to DMSO treatment of this particular isoform (see Table 1). Furthermore, recovery from fast inactivation slows down for the four Nav channel isoforms tested here. All data is shown before (dark) and after addition of 100 mM rufinamide (light) on hNav1.1 (b), hNav1.2 (c), hNav1.3 (d), and hNav1.6 (e); n=5-8 and error bars represent s.e.m.
Figure 5:
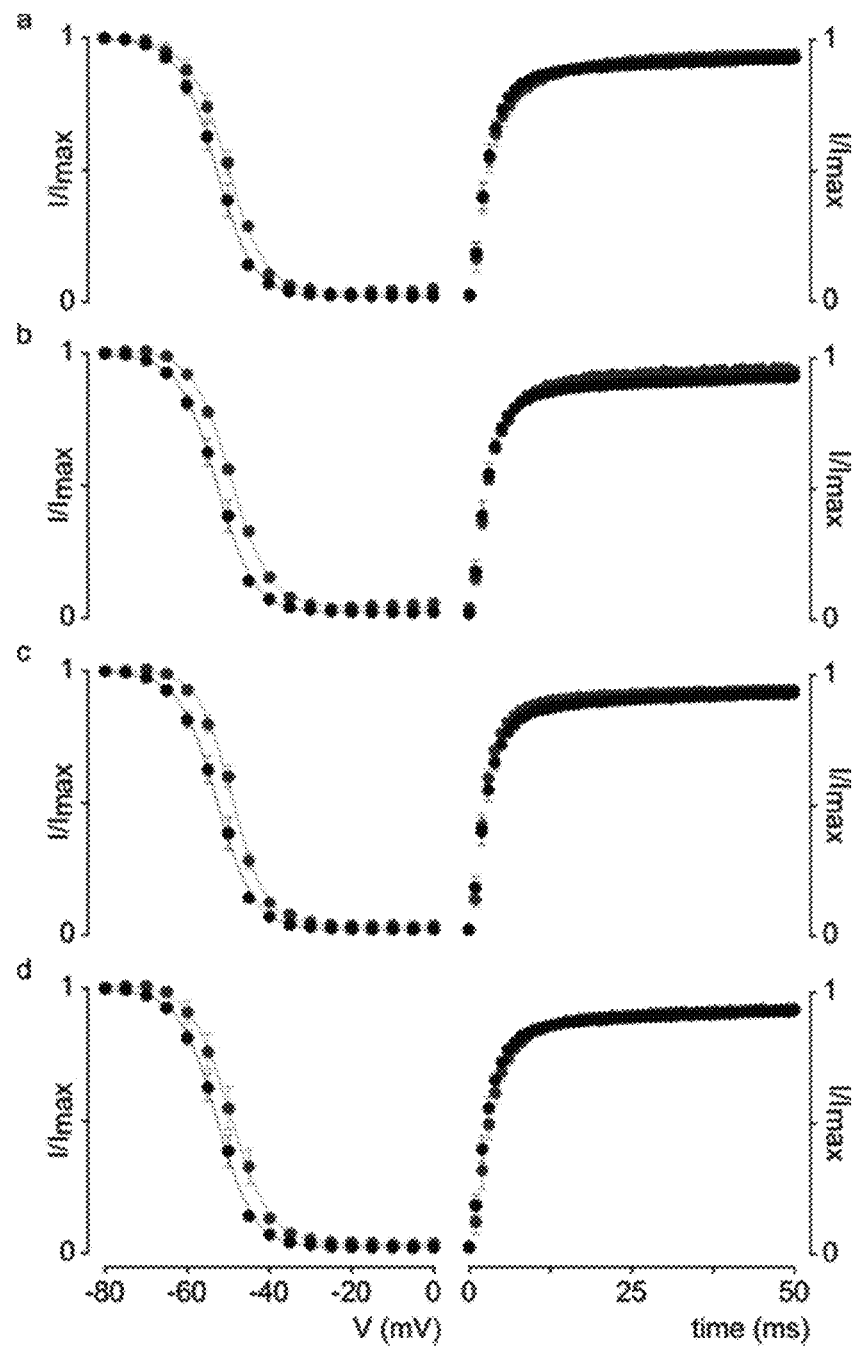
FIG. 5: Effect of rufinamide derivatives on hNav1.1. FIGS. a-d, Left column shows steady-state inactivation (I/Imax) relationships whereas right column displays recovery from fast inactivation determined by a double pulse protocol to Gmax. All data is shown before (dark) and after addition of 100 μM Compound A-D (light) on hNav1.1. No significant differences are observed whereas rufinamide itself does affect recovery from fast inactivation; n=5-8 and error bars represent s.e.m.

After incubating oocytes with 100 μM rufinamide, we observe a dramatic depolarizing shift in the G-V relationship of hNav1.1 whereas the opening of hNav1.2, hNav1.3, and hNav1.6 is not inhibited (FIG. 2, Table 1). In contrast, steady-state inactivation of hNav1.1, hNav1.2, and hNav1.3 is not influenced (FIG. 5, Table 1); however, 100 μM rufinamide does alter the midpoint of hNav1.6 channel availability by about +5 mV (Table 1). Moreover, recovery from fast inactivation slows down for all tested Nav channel isoforms (FIG. 2) and although these effects are subtle, the combination with a substantial shift in hNav1.1 activation voltage may explain a decrease in neuronal excitability after drug administration. Altogether, these experiments with four neuronal Nav channel isoforms suggest that rufinamide primarily targets hNav1.1 opening, an observation that supports a role of this particular Nav channel variant in epilepsy syndromes. It is worth noting that rufinamide may alter hNav1.1 activation by influencing voltage-sensor activation or by slowing subsequent gating transitions, a distinct working mechanism among the classic anticonvulsant drugs since these compounds are thought to exert their effect by 1) occluding the pore to prevent sodium ion flow; or 2) interacting with the inactivated state to decrease the pool of channels available for opening.

Example 3

Figure 3:
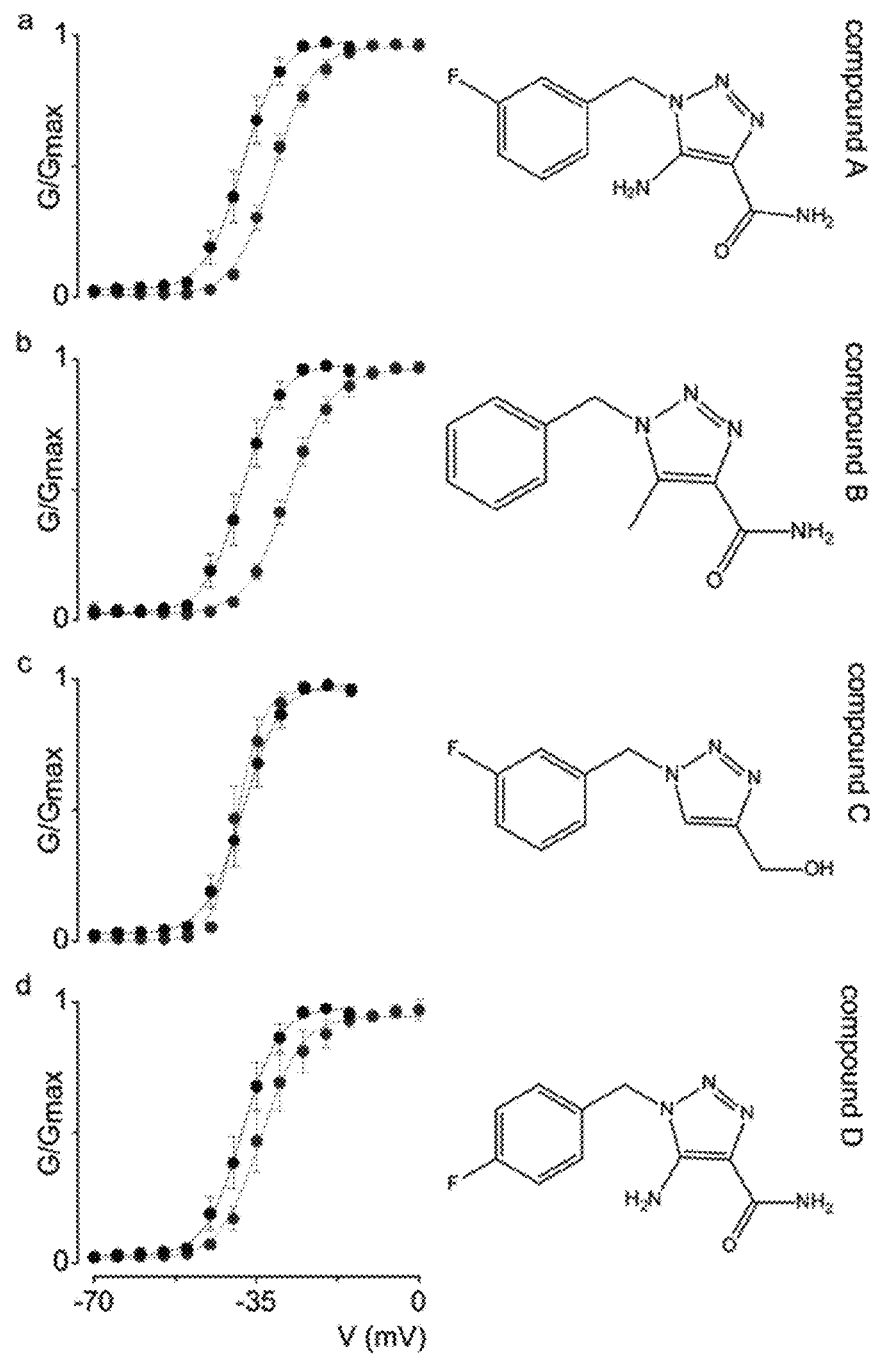
FIG. 3: Effect of rufinamide derivatives on hNav1.1 a-d, Left column shows normalized deduced conductance-voltage (G/Gmax) relationships before (dark) and after (light) addition of rufinamide derivatives fitted with the Boltzmann equation. Compound A, and B clearly inhibit hNav1.1 opening whereas compound C no longer affects hNav1.1 opening (compound D is not significant when considering p<0.005); n=5-8 and error bars represent s.e.m. Right column displays the molecular organization of the four tested derivatives (compounds A-D).
Figure 6:
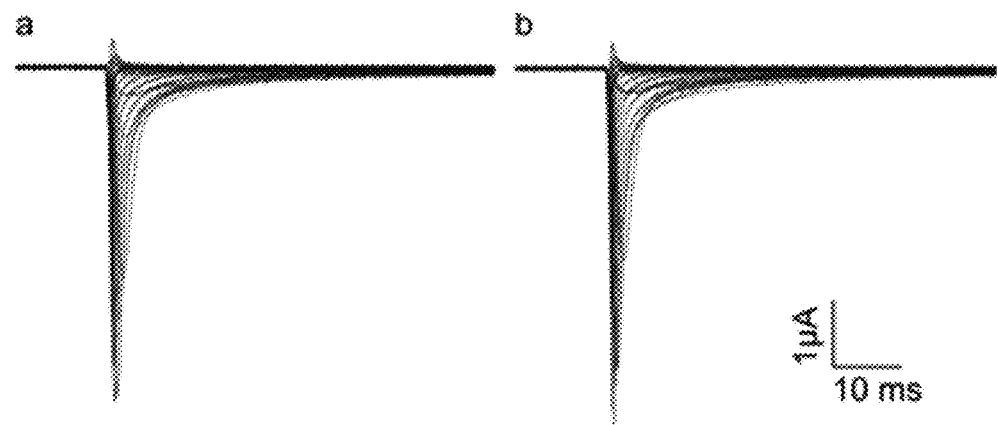
FIG. 6: Rufinamide and compound B do not affect persistent current. Representative example of a family of hNav1.1-mediated sodium currents before (dark) and after (light) addition of 100 μM rufinamide (a) or 100 μM compound B (b). Persistent current was analyzed at the end of a 50 ms test pulse. Drug application did not alter this current component.
Figure 7:
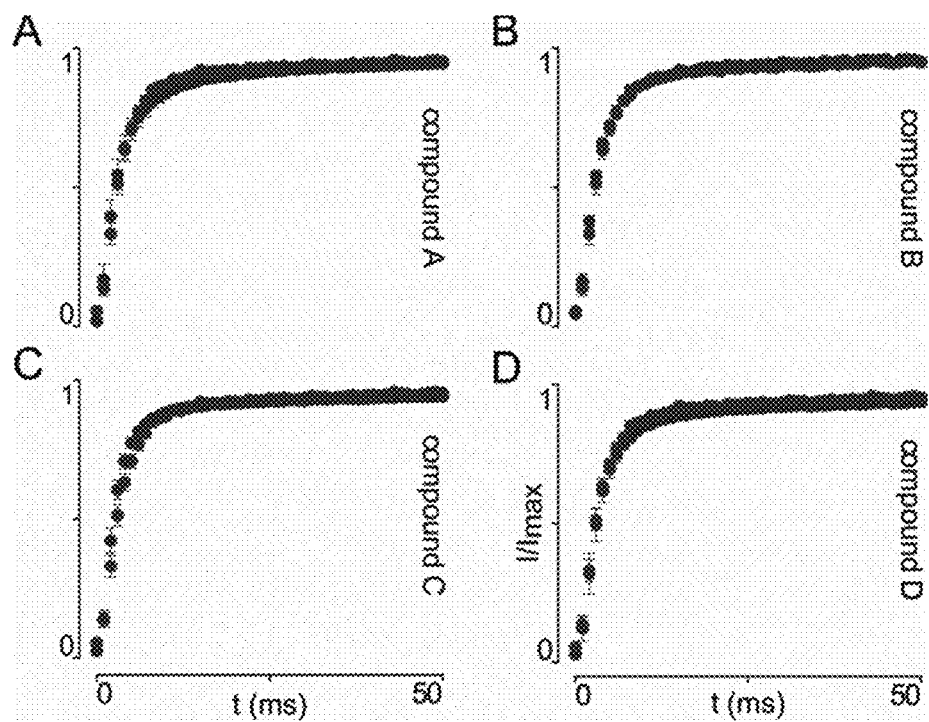
FIG. 7: Effect of rufinamide derivatives on hNav1.1. 7A-D, Figure displays recovery from fast inactivation determined by a double pulse protocol to Gmax. All data is shown before (dark—DMSO control) and after (light) addition of 100 μM Compounds A-D on hNav1.1 (a-d). No significant differences are observed whereas rufinamide itself does affect recovery from fast inactivation (see FIG. 1).
Figure 8:
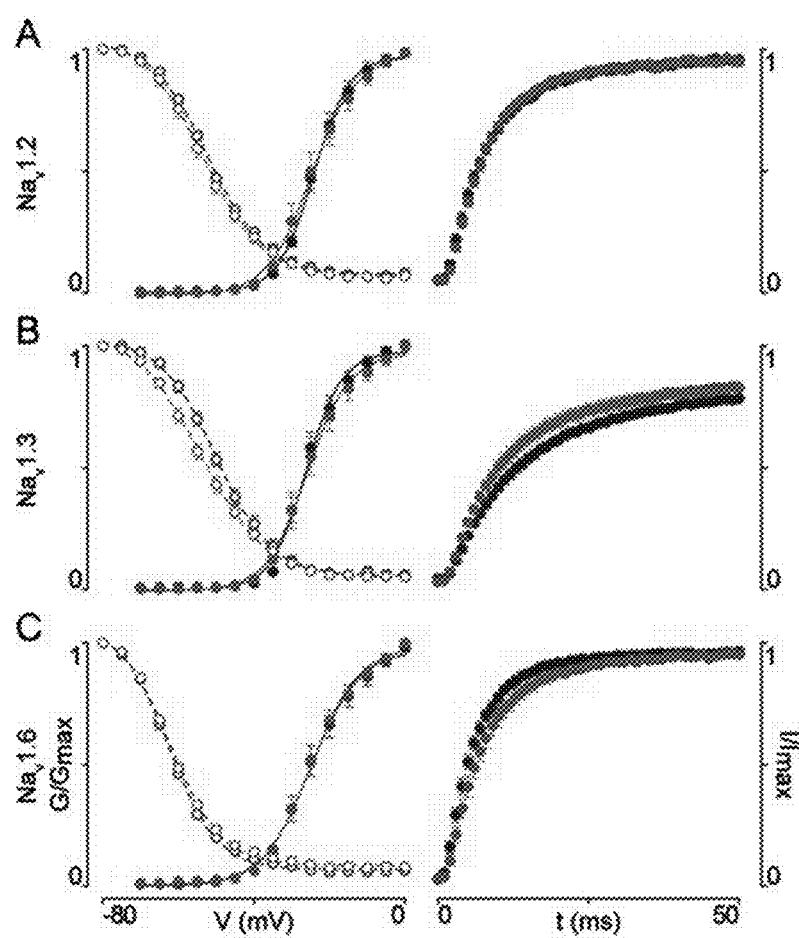
FIG. 8: Compound B does not influence the tested gating properties of other neuronal Nav channel isoforms. 8A-C, left column shows normalized deduced conductance-voltage (G/Gmax) and steady-state inactivation (I/Imax) relationships whereas right column displays recovery from fast inactivation determined by a double pulse protocol (1-50 ms) to Gmax. All data is shown before (dark—DMSO control) and after (light) addition of 100 μM Compound B on hNav1.2 (A), hNav1.3 (B), and hNav1.6 (C). Fit values are reported in Table 2. n=5-8 and error bars represent s.e.m.

Molecular modifications of rufinamide enhance hNav1.1 efficacy. The triazole-derived molecular organization of rufinamide is distinct among anti-epileptic compounds. To examine which features of the N-benzyl triazole core are important for its inhibitory action on hNav1.1, four structurally related compounds with unknown functionality were selected and a structure-activity relationship (SAR) study was performed using 1-[(3-fluorophenyl)methyl]-1H-1,2,3-Triazole-4-carboxamide-5-amine (Compound A); 1-[phenyl-methyl]-1H-1,2,3-Triazole-4-carboxamide-5-methyl (Compound B); 1-[(3-fluorophenyl)methyl]-1H-1,2,3-Triazole-4-hydroxymethyl (Compound C); and 1-[(4-fluorophenyl)methyl]-1H-1,2,3-Triazole-4-carboxamide-5-amine (Compound D). As a result, we found that Compound A and B inhibit hNav1.1 opening (FIG. 3; Table 1), with Compound B producing the largest depolarizing shift in channel activation voltage (~+11 mV). Strikingly, neither of these compounds influences hNav1.1 steady-state inactivation, recovery from inactivation or persistent current (FIGS. 6, 7, Table 1), suggesting a working mechanism geared towards stabilizing the closed state of the channel. In contrast to rufinamide, application of 100 μM Compound B selectively modulates hNav1.1 activation whereas the tested gating parameters of hNav1.2, hNav1.3, and hNav1.6 are unaltered (FIG. 8, Table 2).

TABLE 2

Lack of effect of Compound B on the tested gating properties of hNav1.2, hNav1.3, and hNav1.6.

|  |  | hNa$_v$1.2 | hNa$_v$1.3 | hNa$_v$1.6 |
|---|---|---|---|---|
| Compound B | Activation (V$_{1/2}$) | −23.6 ± 1.1 mV | −25.8 ± 1.4 mV | −23.8 ± 1.9 mV |
|  | Inactivation (V$_{1/2}$) | −53.6 ± 1.2 mV | −50.0 ± 0.8 mV | −62.6 ± 0.7 mV |
|  | Recovery (T) | 8.2 ± 0.3 ms | 13.7 ± 0.6 ms | 6.1 ± 0.4 ms |

Figure 9:
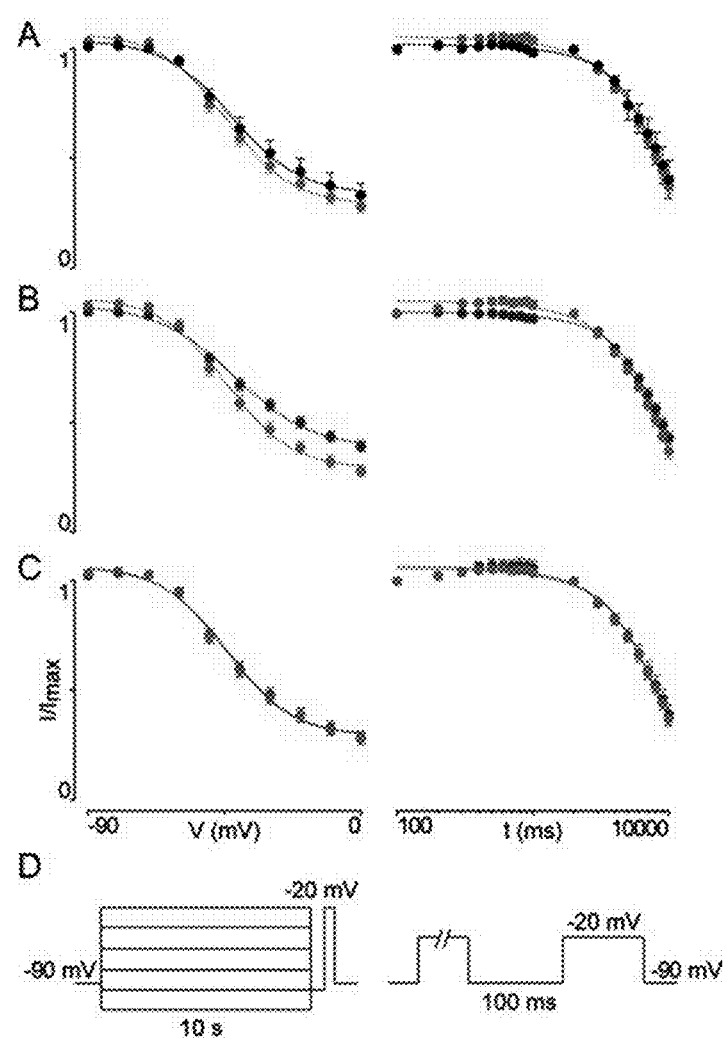
FIG. 9: Rufinamide and Compound B do not influence hNav1.1 slow inactivation. Left column shows normalized current-voltage relationships (I/Imax) for the voltage-dependence of slow inactivation, fitted with a standard Boltzmann function. Right column shows normalized current-time relationships (I/Imax) for time-dependence of entry into slow inactivation, fitted with a single exponential curve. (9A) compares control oocytes (dark circle) to DMSO-treated oocytes (light circle), (9B) DMSO (light circle) vs. rufinamide (dark circle), and (9C) DMSO (light circle) vs. Compound B (dark circle). (9D) illustrates the voltage protocol used in each of the two experiments. All recordings were made from oocytes expressing hNav1.1. Fit values reported in Table 3. n=3-5 and error bars represent s.e.m.
Figure 10:
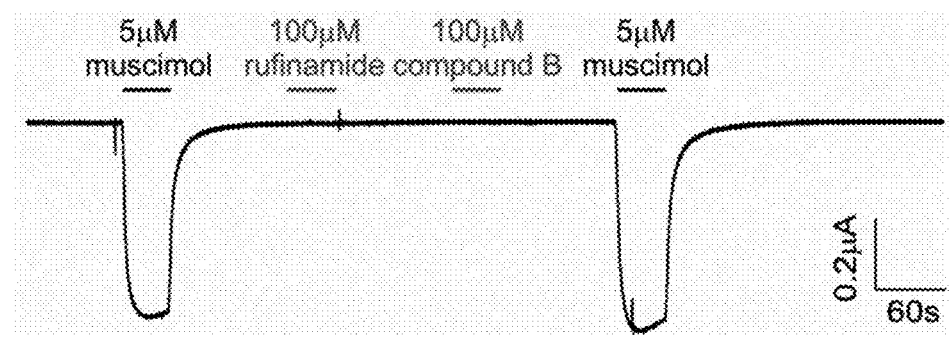
FIG. 10: Rufinamide and Compound B do not activate the α1/β2/γ2 GABA$_A$ receptor. Application of 5 µM muscimol activates the α1/β2/γ2 GABA$_A$ receptor as seen in the first and last pulse whereas 100 µM rufinamide and Compound B do not evoke inward GABA$_A$-mediated currents. Oocytes were kept at −70 mV throughout the experiment.
Figure 11:
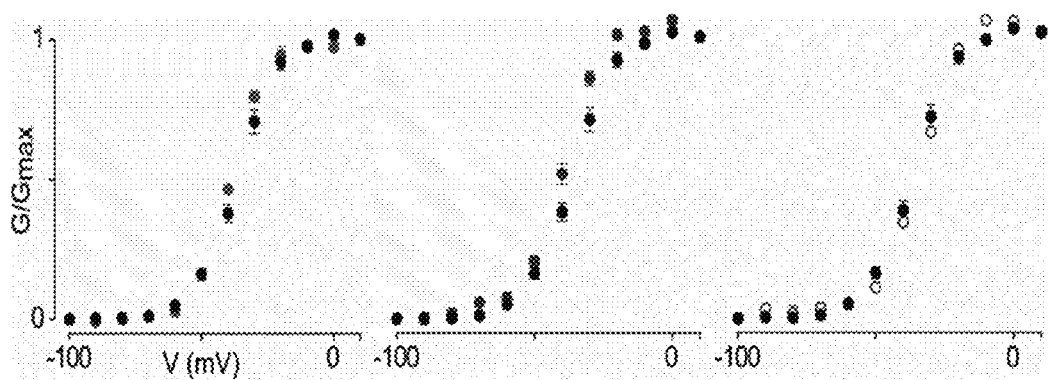
FIG. 11: Rufinamide and compound B do not inhibit hERG channels. Normalized conductance-voltage (G/Gmax) relationships of hERG channels determined by voltage steps from −100 mV to +50 mV in 10 mV increments for 2 seconds followed by a pulse to −60 mV for 2 seconds from an oocyte holding potential of −90 mV. Shown are control (black solid circles) in the presence of 1% DMSO (dark circles), 100 µM rufinamide (light circles), and 100 µM Compound B (open circles). n=3-4 and error bars represent s.e.m.

Moreover, the results show that rufinamide and compound B do not influence entry or voltage-dependence of hNav1.1 slow inactivation (FIG. 9, Table 3). Finally, rufinamide and Compound B (100 μM) do not activate the α1/β2/γ2 GABA$_A$ receptor (FIG. 10), a subtype ubiquitously found in GABAergic neurons that is targeted by psychoactive drugs such as zolpidem and benzodiazepines. Also, neither drug inhibits hERG, a member of the cardiac potassium channel family and an FDA-mandated screening target for potential off-target drug effects (FIG. 11).

TABLE 3

Rufinamide and Compound B do not influence hNav1.1 slow inactivation.

|  |  | Voltage-dependence of SI (V) | Entry into SI (T) |
|---|---|---|---|
| V$_{1/2}$ or t | Control | −41.5 ± 1.6 mV | 6.2 ± 0.4 s |
|  | DMSO | −43.7 ± 1.6 mV | 5.6 ± 0.3 s |
|  | Rufinamide | −41.1 ± 1.5 mV | 6.2 ± 0.3 s |
|  | Compound B | −43.2 ± 1.3 mV | 5.5 ± 0.4 s |

Figure 12:
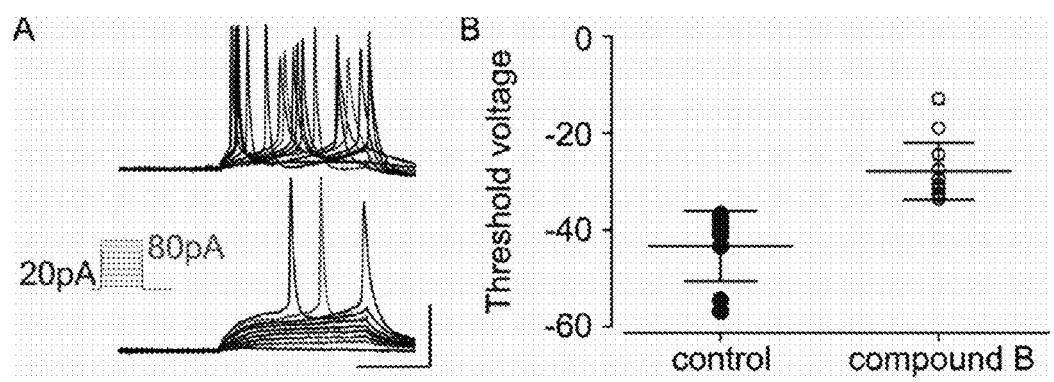
FIG. 12: Effect of Compound B on rat hippocampal neurons. 12A, Representative recordings of cells treated with DMSO-containing vehicle (left) versus cells treated with Compound B (right). Inset shows the current clamp protocol of a series of 10 pA depolarizing current injections in which light and dark colors indicate the current needed to elicit an action potential in control conditions (20 pA) versus the treated cells (80 pA). 12B, Average action potential thresholds are significantly higher in cells treated with Compound B (−27.8±1.6 mV, open circles, n=7) compared with cells treated with DMSO-containing vehicle (−43.3±2.4 mV, closed circles, n=7).

One of the most fascinating results obtained from these SAR studies is that Compound B inhibits hNav1.1 more efficaciously when compared to rufinamide (FIG. 12, Table 1). The identification of such a molecule is particularly exciting as it underlines the immense scope of rufinamide scaffold-based drug development for treating epilepsy disorders involving aberrant hNav1.1 behavior. When comparing the structures of rufinamide and Compound B, two differences stand out. On the one hand, rufinamide has two electron-withdrawing fluoro substituents on the phenyl group whereas Compound B has none thereby rendering the phenyl group of this molecule more electron-rich. On the other hand, there is an additional methyl substituent on the triazole ring in compound B, resulting in an increased hydrophobic character when compared to rufinamide. Another important observation from our experiments is that Compound C does not influence hNav1.1 gating (FIG. 12). The most significant structural feature of this molecule is the presence of a methylene hydroxyl (—CH$_2$OH) group on its triazole moiety whereas an amide (CONH$_2$) substituent is found within the other compounds.

Example 4

Compound B increases the action potential threshold in hippocampal neurons. Nav1.1 distribution is strikingly similar in human to rodent brains. Moreover, 99% of the amino acids that make up Nav1.1 are conserved between humans, rats, and mice. As such, it was expected that the inhibitory effect of Compound B would increase the action potential threshold in Nav1.1-expressing rat hippocampal neurons. To test this hypothesis, a physiological solution containing 100 μM Compound B was applied to cultured hippocampal neurons and found that a current injection of 80 pA elicits an action potential (FIG. 12A). In contrast, hippocampal neurons in control conditions require a current injection of only 20 pA to start generating action potentials (FIG. 12A). When assessing average firing thresholds by calculating the potential at which the rate of rise crosses 40V/s, a value of −43.3±2.4 mV was observed for control cells whereas −27.8±1.6 mV is noted when cells are treated with 100 μM Compound B (FIG. 12B). Altogether, these results suggest an ability of Compound B to reduce action potential firing in hippocampal neurons by shifting the firing threshold in the depolarizing direction, possibly by deferring Nav1.1 channel activation to more positive membrane voltages (FIG. 2B, FIG. 8, and Table 1).

Example 5

Figure 13:
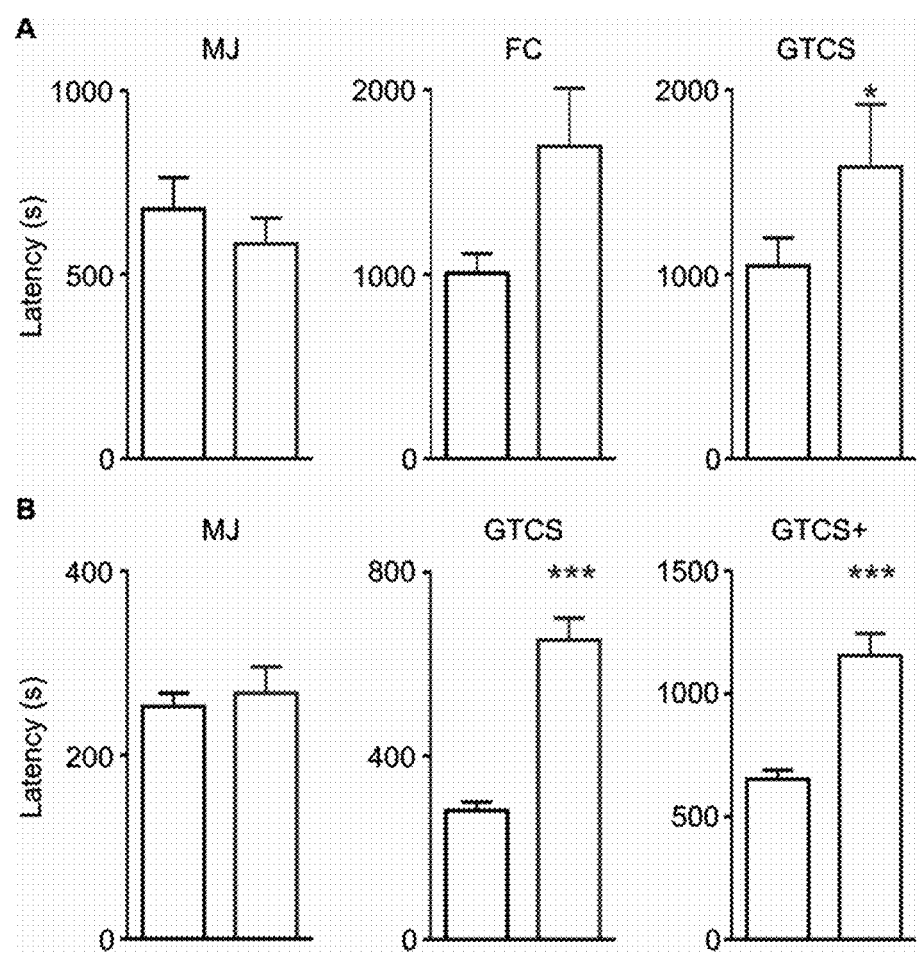
FIG. 13: Compound B increases latencies to picrotoxin- and flurothyl-induced generalized seizures. 13A, Picrotoxin (10 mg/kg) was administrated to vehicle-(dark) and Compound B-treated (light) male Crl:CF1 mice 15 minutes prior to seizure induction. The average latencies in seconds to the first myoclonic jerk (MJ), forelimb clonus (FC), and generalized tonic-clonic seizure (GTCS) are compared. Compound B increases the average latency to the first GTCS. *p<0.05. Error bars represent s.e.m. 13B, The latencies to the MJ, GTCS, and GTCS with hind limb extension (GTCS+) in the flurothyl model are compared between vehicle-(dark) and Compound B-treated (light) male Crl:CF1 mice. The average latencies in seconds to the GTCS and GTCS+ are significantly longer in the Compound B-treated mice. ***p<0.001. Error bars represent s.e.m.

Compound B is effective in rodent seizure induction paradigms. First, Compound B was tested in the picrotoxin seizure induction assay, a widely used epilepsy model based on inhibiting GABA-mediated synaptic transmission. Based on the effective dose of rufinamide reported before, Compound B was tested at 75 mg/kg. Even though the forelimb clonus (FC) tends to occur later in the Compound B-treated mice, no statistically significant differences were observed between vehicle- and Compound B-treated mice in their average latencies to the first myoclonic jerk (MJ) (p=0.4) and FC (p=0.3) (FIG. 13). However, the average latency to the first generalized tonic-clonic seizure (GTCS) following treatment with Compound B is significantly increased by 41% (1693±315s, p=0.03) when compared to vehicle-treated mice (1006±106s). There is no difference in the frequency of the behavioral seizures between the treatment groups.

Since one assay may not accurately reflect the ability of a drug to increase seizure resistance, the efficacy Compound B was tested using the flurothyl paradigm, an established seizure induction model involving animal exposure to the volatile pro-convulsant bis-2,2,2-trifluoroethyl ether. Although the average latency to the MJ is comparable between vehicle- and compound B-treated mice (p=0.6), the average latencies to the first GTCS and GTCS with hind limb extension (GTCS+) are increased by 43% and 56%, respectively (p<0.0001; GTCS: 652±48s; GTCS+: 1155±89s), when compared to the vehicle-treated group (281±19s and 652±38s, respectively) (FIG. 13). These results clearly demonstrate that Compound B successfully increases the average latency to flurothyl-induced GTCS and GTCS+.

Figure 14:
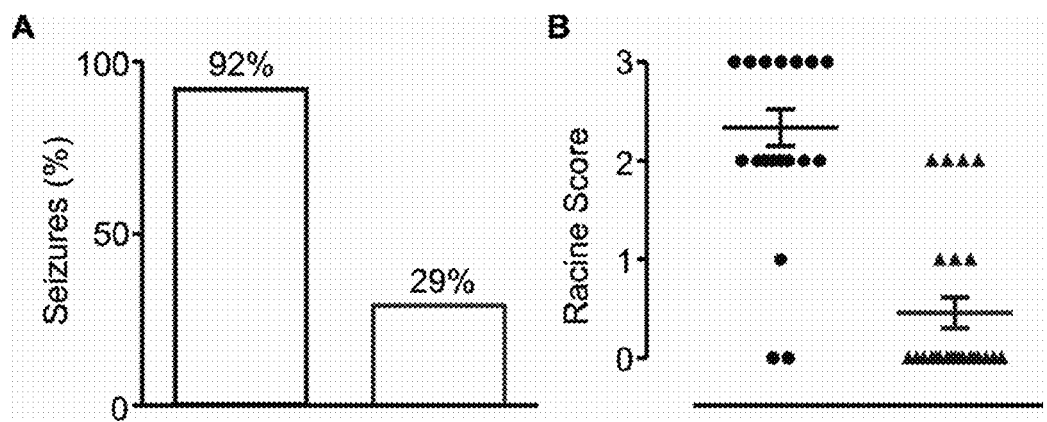
FIG. 14: Compound B reduces the severity of seizures induced by the 6 Hz psychomotor paradigm. 14A current intensity of 17 mA was used to induce partial seizures in vehicle-(dark) and Compound B-treated (light) male Crl:CF1 mice. Following treatment with Compound B, there is a 63% reduction in the number of mice exhibiting seizures (14A; p<0.0001). In addition, the seizures that were observed in the Compound B-treated (light) mice are typically less severe than those seen in the vehicle treated mice (dark) (14B; p<0.0001). Error bars represent s.e.m.

Finally, Compound B was examined to determine whether it is capable of reducing the occurrence and severity of seizures observed in the 6 Hz seizure induction paradigm, a model with a proven track record in drug development (*Epilepsy Res* 47, 217-227 (2001)). At a current intensity of 17 mA, 92% (n=22/24) of vehicle treated mice display behavioral seizures and the majority of the observed seizures can be characterized as forelimb clonus (Racine score=2) or rearing and falling (Racine score=3) (FIG. 14). In sharp contrast, only 29% (n=7/24, p<0.0001) of the Compound B-treated animals exhibit behavioral seizures, which are also dramatically less severe compared to those seen in the vehicle-treated mice (p<0.0001). Overall, these results substantiate that it is possible to achieve seizure resistance by modifying the N-benzyl triazole scaffold of rufinamide to target hNav1.1 activation.

Example 6

Compounds which specifically target hNav1.1 sodium channels.

Figure 15:
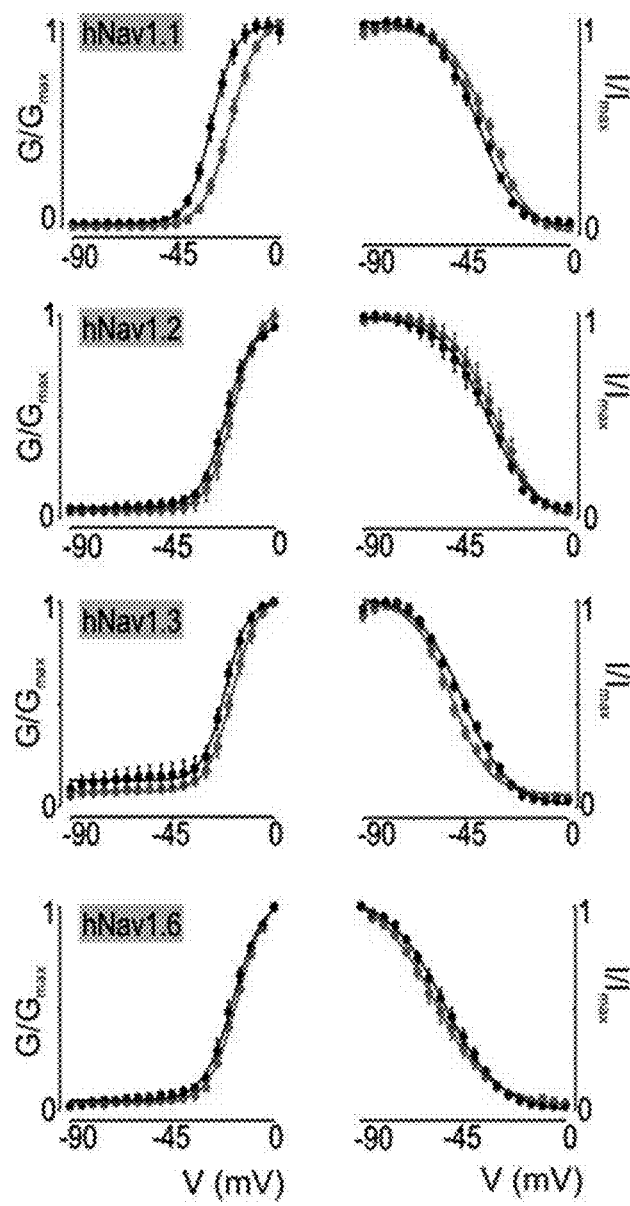
FIG. 15: Effects of Compound F on hNav1.1 channels.

Compound F, 1-(phenylmethyl)-1H-1,2,3-triazole-4-carboxamide-5-ethyl, also selectively targets hNav1.1 through a similar mechanism as Compound B (FIG. 15). In particular, we found that Compound F inhibits hNav1.1 opening by producing a substantial depolarizing shift in channel activation voltage (~+12 mV). Strikingly, this compound does not influence hNav1.1 steady-state inactivation, recovery from inactivation, or persistent current, suggesting a working mechanism geared towards stabilizing a closed state of this particular Nav channel isoform. Intrigued by the unique molecular organization of Compound F compared to rufinamide, we examined which features of the N-benzyl triazole core contribute most to its selective inhibitory effect on hNav1.1. As a result, three important features that need to be considered for hNav1.1 drug development using the N-benzyl triazole scaffold emerge from our study. First, tweaking the electron density of the phenyl ring by removing or repositioning electron withdrawing fluoro groups is an important strategy. Second, increasing the hydrophobicity of the triazole ring (by introducing alkyl substituents at position 5) results in molecules with improved hNav1.1 efficacy and selectivity. Third, an amide substituent on the triazole ring plays an important role in imparting hNav1.1 selectivity to triazole analogs.

Example 7

Compounds which specifically target hNav1.6 sodium channels.

As stated above, the present inventors previously identified another compound, Compound B with which the inventors obtained specific inhibition of hNav1.1 activation thereby increasing seizure thresholds in rodent models of epilepsy. In contrast to rufinamide which primarily influences the voltage-dependence of hNav1.1 activation and availability of hNav1.6 channels whereas the recovery from fast inactivation of hNav1.1, hNav1.2, hNav1.3, and hNav1.6 is only slightly altered, Compound B selectively modifies hNav1.1 opening without affecting other CNS Nav channels, GABAa receptors, or hERG. One of our inventive compounds Compound L, 1-[(2,6-difluorophenyl)methyl]-1H-1,2,3-triazole-carboxymethyl-5-methyl, also targets hNav1.1 through a similar mechanism as Compound B (FIG. 16). However, the effect is much smaller compared to compound B. In contrast, Compound L drastically shifts hNav1.6 steady-state inactivation to more hyperpolarized potentials (~-20 mV), thereby decreasing the number of hNav1.6 channel that can be activated during membrane depolarization (FIG. 16). In effect, this compound reduces hNav1.6 currents which may be beneficial for treating particular disorders. Intrigued by the unique molecular organization of our lead compound compared to rufinamide, we examined which features of the N-benzyl triazole core contribute most to its selective inhibitory effect on hNav1.6.

As a result, three important features that need to be considered for hNav1.6 drug development using the N-benzyl triazole scaffold emerge from our study. First, tweaking the electron density of the phenyl ring by adding or repositioning electron withdrawing fluoro groups is an important strategy. Second, decreasing the hydrophobicity of the triazole ring (by removing alkyl substituents at position 5) results in molecules with improved hNav1.6 efficacy and selectivity. Third, a carboxymethyl substituent on the triazole ring plays an important role in imparting hNav1.6 selectivity to triazole analogs.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for inhibition of the activation of one or more voltage-gated sodium hNav1.1 or hNav1.6 channels in one or more neurons of a subject comprising administering to the subject an effective amount of a compound selected from the group consisting of:

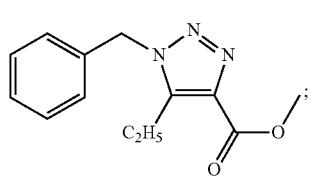

(Compound E)

(Compound H)

(Compound I)

(Compound J)

(Compound K)

(Compound L)

(Compound M)

(Compound N)

(Compound O)

(Compound P)

(Compound Q)

or a salt, solvate, or stereoisomer thereof.

2. The method of claim 1, wherein the one or more voltage-gated sodium (Nav) channels are hNav1.1 channels.

3. The method of claim 1, wherein the one or more voltage-gated sodium (Nav) channels are hNav1.6 channels.

4. A method for treating a seizure disorder in a subject comprising administering to the subject an effective amount of a compound selected from the group consisting of:

(Compound E)

(Compound H)

(Compound I)

(Compound J)

(Compound K)

-continued (Compound L)
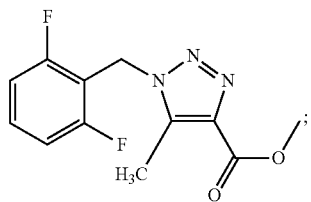

(Compound M)
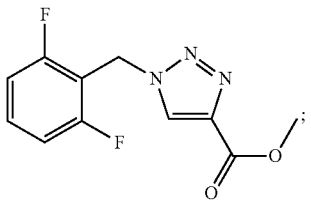

(Compound N)
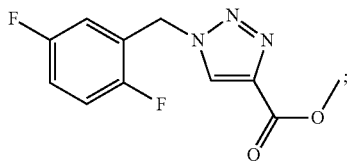

(Compound O)
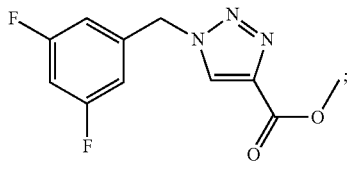

(Compound P)
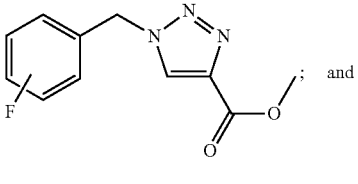

; and (Compound Q)
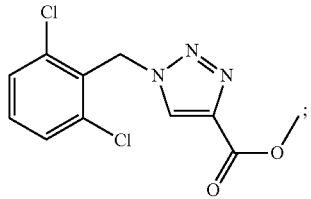

or a salt, solvate, or stereoisomer thereof.

5. The method of claim 4, wherein the seizure disorder is epilepsy.

6. The method of claim 4, wherein the epilepsy disorder is Lennox-Gastaut Syndrome (LGS).

7. A method for treating an anxiety disorder in a subject comprising administering to the subject an effective amount of a compound selected from the group consisting of:

(Compound E)
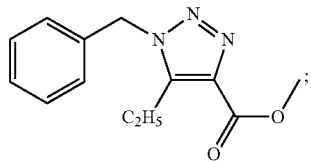

-continued (Compound H)
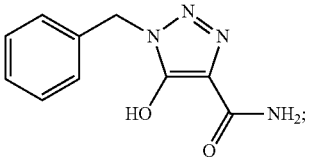

(Compound I)
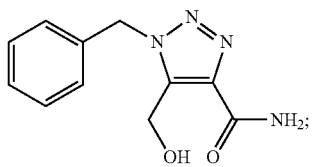

(Compound J)
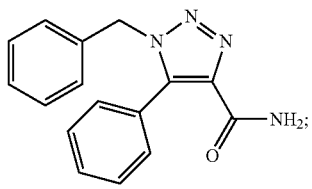

(Compound K)
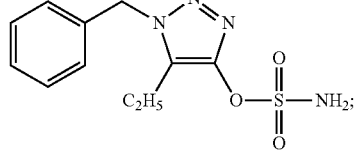

(Compound L)
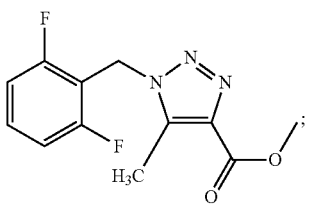

(Compound M)
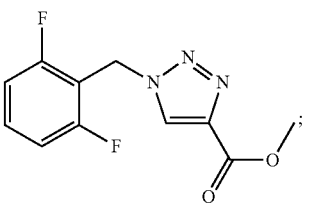

(Compound N)
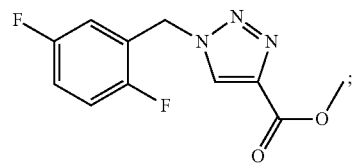

(Compound O)
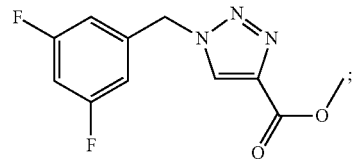

(Compound P)

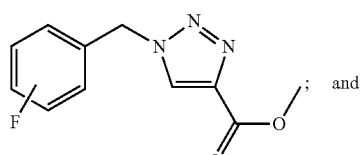

; and (Compound Q)

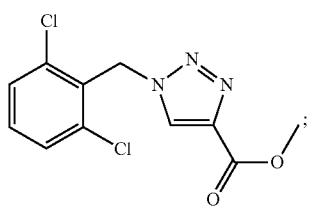

;

or a salt, solvate, or stereoisomer thereof.

8. The method of claim 7, wherein the anxiety disorder is post-traumatic stress disorder.

9. A method for treating migraine in a subject comprising administering to the subject an effective amount of a compound selected from the group consisting of:

(Compound E)

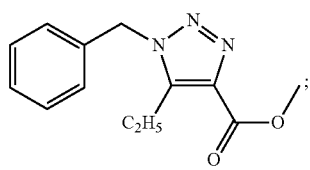

;

(Compound H)

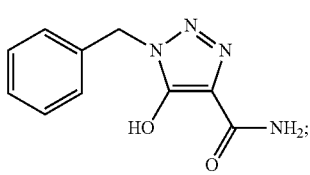

;

(Compound I)

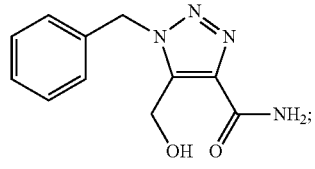

;

(Compound J)

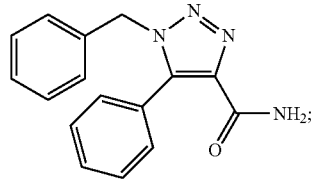

;

(Compound K)

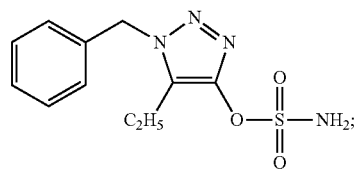

;

(Compound L)

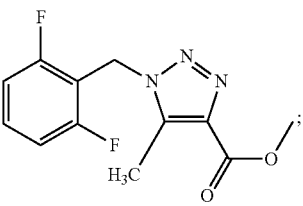

;

(Compound M)

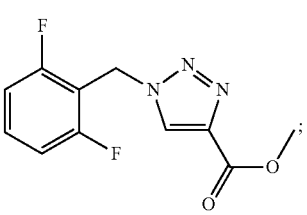

;

(Compound N)

;

(Compound O)

;

(Compound P)

; and (Compound Q)

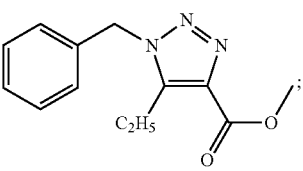

;

or a salt, solvate, or stereoisomer thereof.

10. A method for treating neuropathic pain in a subject comprising administering to the subject an effective amount of a compound selected from the group consisting of:

(Compound E)

;

-continued (Compound H)
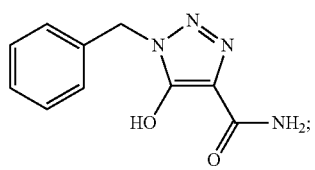

(Compound I)
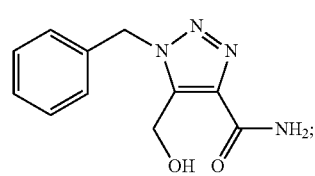

(Compound J)
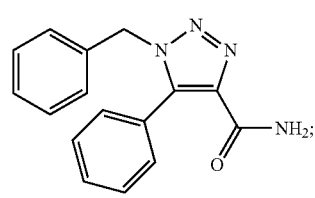

(Compound K)
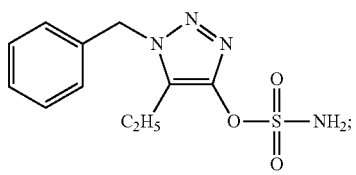

(Compound L)
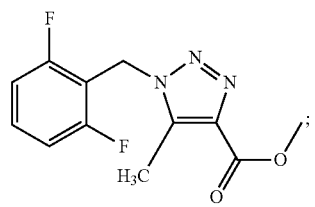

(Compound M)
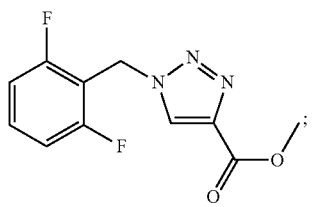

(Compound N)
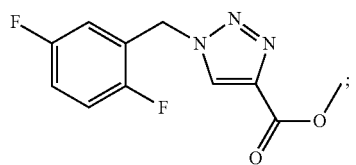

(Compound O)
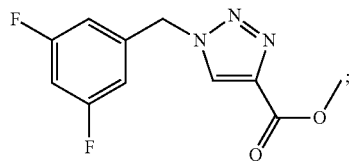

-continued (Compound P)
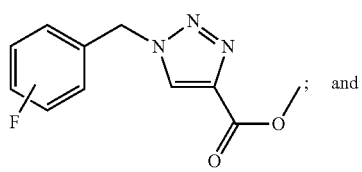

(Compound Q)
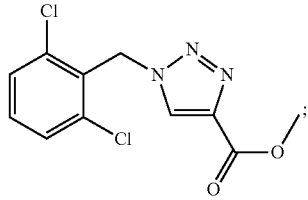

or a salt, solvate, or stereoisomer thereof.

11. The method of claim 10, wherein the neuropathic pain is caused by Diabetes.

12. A method for inhibition of the activation of one or more voltage-gated sodium hNav1.1 or hNav1.6 channels in one or more neurons of a subject comprising administering to the subject an effective amount of a pharmaceutical composition selected from the group consisting of:

(Compound E)
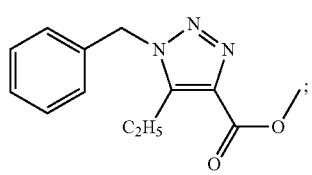

(Compound H)
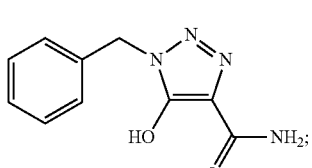

(Compound I)
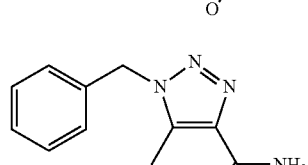

(Compound J)
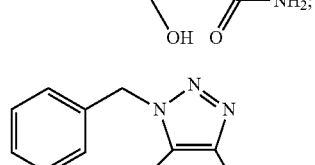

(Compound K)
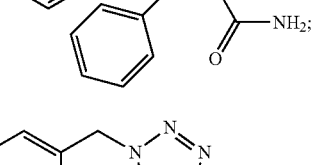

-continued (Compound L)
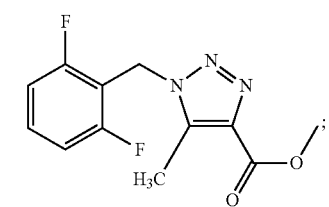

(Compound M)
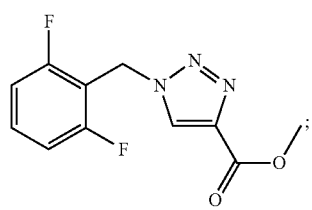

(Compound N)
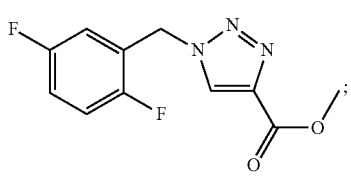

(Compound O)
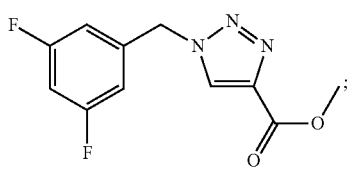

(Compound P)
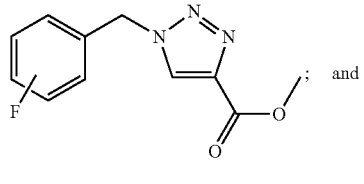

; and (Compound Q)
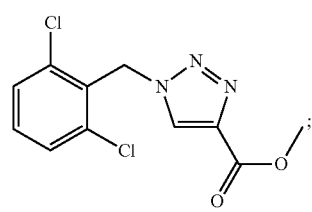

or a salt, solvate, or stereoisomer thereof, and a pharmaceutically acceptable carrier.

13. The method of claim 12, wherein the one or more voltage-gated sodium (Nav) channels are hNav1.1 channels.

14. The method of claim 12, wherein the one or more voltage-gated sodium (Nav) channels are hNav1.6 channels.

15. A method for treating a seizure disorder in a subject comprising administering to the subject an effective amount of a pharmaceutical composition selected from the group consisting of:

(Compound E)
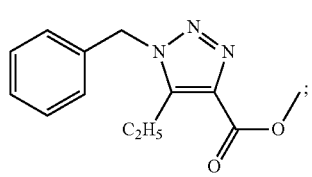

(Compound H)
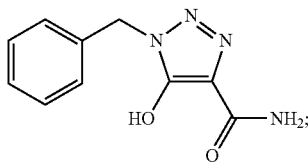

(Compound I)
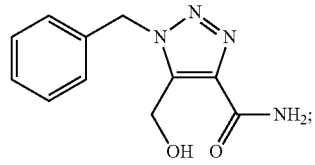

(Compound J)
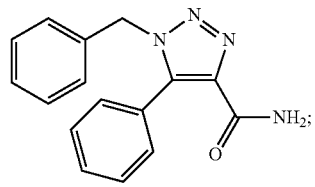

(Compound K)
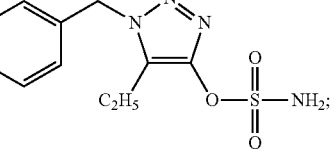

(Compound L)
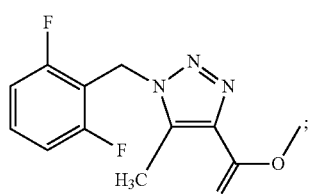

(Compound M)
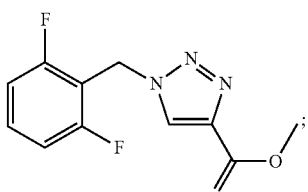

(Compound N)
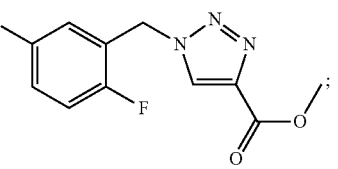

-continued

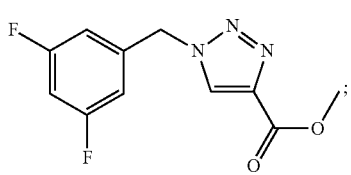
(Compound O)

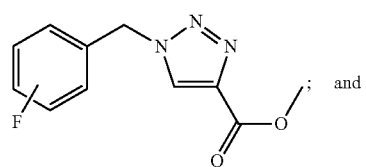
(Compound P)

and

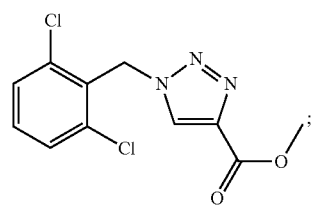
(Compound Q)

or a salt, solvate, or stereoisomer thereof, and a pharmaceutically acceptable carrier.

16. The method of claim 15, wherein the seizure disorder is epilepsy.

17. The method of claim 15, wherein the epilepsy disorder is Lennox-Gastaut Syndrome (LGS).

18. A method for treating an anxiety disorder in a subject comprising administering to the subject an effective amount of a pharmaceutical composition selected from the group consisting of:

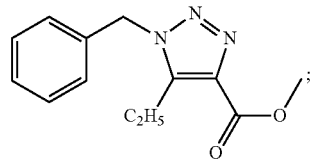
(Compound E)

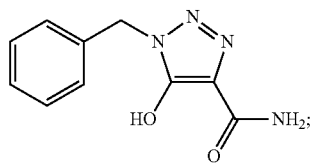
(Compound H)

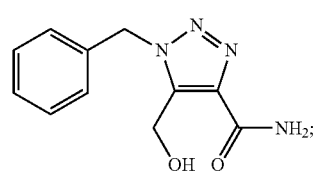
(Compound I)

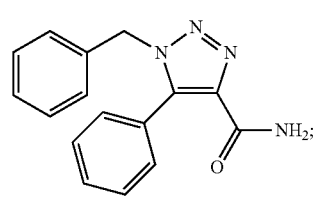
(Compound J)

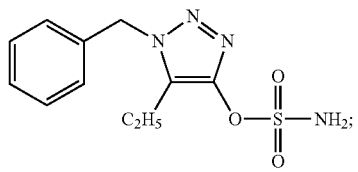
(Compound K)

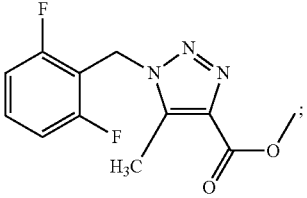
(Compound L)

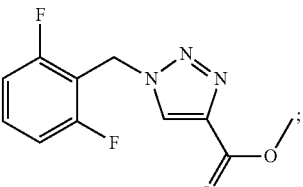
(Compound M)

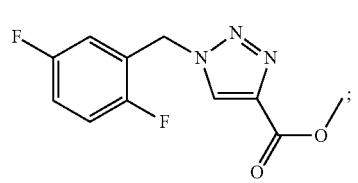
(Compound N)

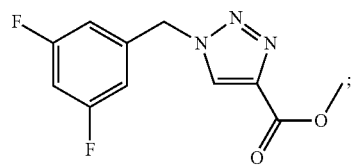
(Compound O)

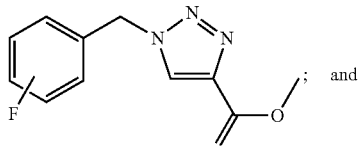
(Compound P)

and

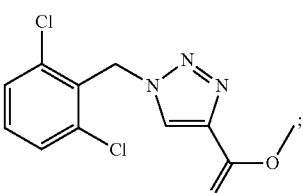
(Compound Q)

or a salt, solvate, or stereoisomer thereof, and a pharmaceutically acceptable carrier.

19. The method of claim 18, wherein the anxiety disorder is post-traumatic stress disorder.

20. A method for treating migraine in a subject comprising administering to the subject an effective amount of a pharmaceutical composition selected from the group consisting of:

(Compound E)
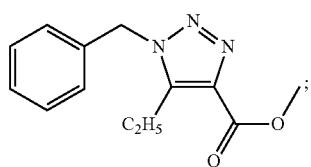

(Compound H)
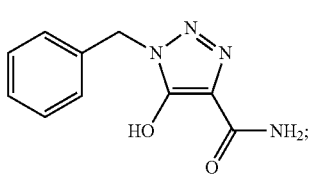

(Compound I)
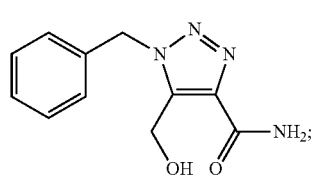

(Compound J)
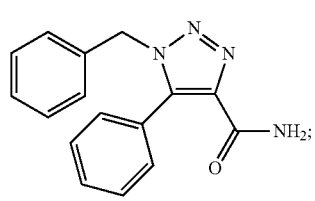

(Compound K)
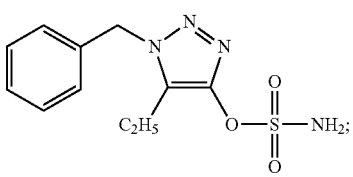

(Compound L)
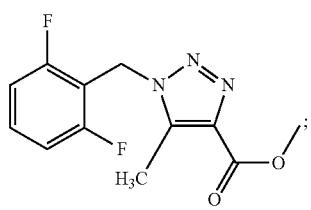

(Compound M)
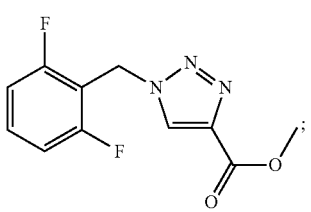

(Compound N)
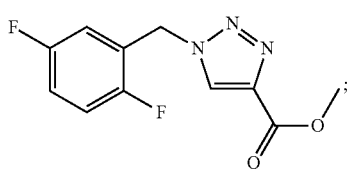

(Compound O)
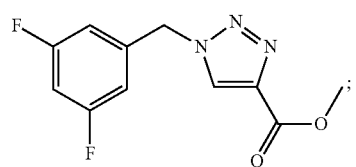

(Compound P)
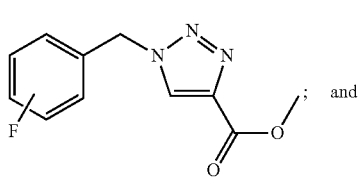
and (Compound Q)
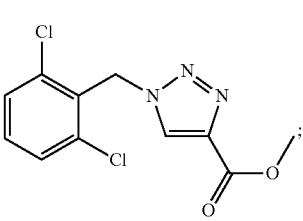

or a salt, solvate, or stereoisomer thereof, and a pharmaceutically acceptable carrier.

21. A method for treating neuropathic pain in a subject comprising administering to the subject an effective amount of a pharmaceutical composition selected from the group consisting of:

(Compound E)
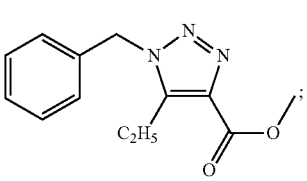

(Compound H)
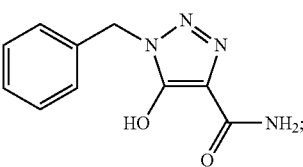

(Compound I)
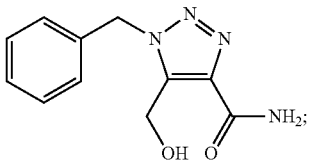

(Compound J)
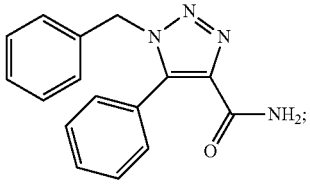

-continued
(Compound K)
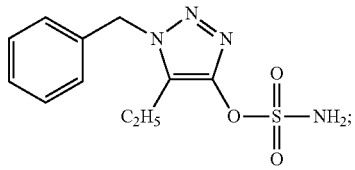
(Compound L)
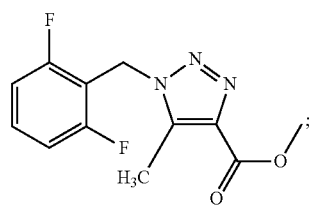
(Compound M)
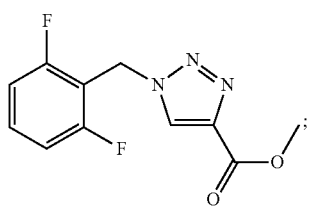
(Compound N)
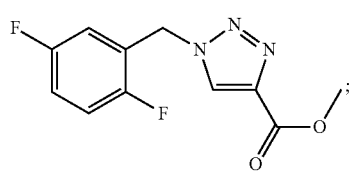
-continued
(Compound O)
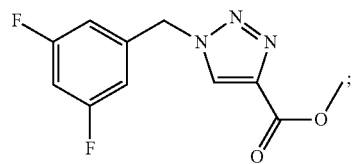
(Compound P)
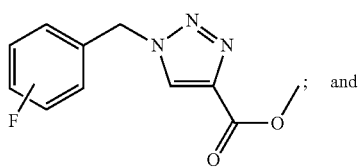
and
(Compound Q)
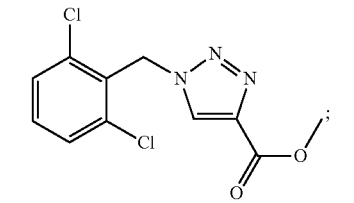
or a salt, solvate, or stereoisomer thereof, and a pharmaceutically acceptable carrier.
22. The method of claim 21, wherein the neuropathic pain is caused by Diabetes.
* * * * *